US010337985B2

(12) United States Patent
Nakajima

(10) Patent No.: US 10,337,985 B2
(45) Date of Patent: Jul. 2, 2019

(54) MEASUREMENT METHOD AND MEASUREMENT SYSTEM

(71) Applicant: Arkray, Inc., Kyoto (JP)

(72) Inventor: Shinya Nakajima, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 350 days.

(21) Appl. No.: 15/095,621

(22) Filed: Apr. 11, 2016

(65) Prior Publication Data
US 2016/0305866 A1    Oct. 20, 2016

(30) Foreign Application Priority Data

Apr. 14, 2015   (JP) ................. 2015-082191

(51) Int. Cl.
*G01N 1/38* (2006.01)
*G01N 21/27* (2006.01)
(Continued)

(52) U.S. Cl.
CPC ..... *G01N 21/274* (2013.01); *G01N 33/48792* (2013.01); *G01N 33/493* (2013.01); *G01N 33/5306* (2013.01); *G01N 35/00603* (2013.01); *G01N 35/00623* (2013.01); *G01N 35/00693* (2013.01); *G01N 1/38* (2013.01); *G01N 2035/00326* (2013.01)

(58) Field of Classification Search
CPC ........... G01N 21/274; G01N 35/00603; G01N 35/00623; G01N 35/00693; G01N 33/48792; G01N 33/493; G01N 33/5306; G01N 1/38; G01N 2035/00326
See application file for complete search history.

(56) References Cited

U.S. PATENT DOCUMENTS

2007/0243559 A1    10/2007   Gunzer et al.
2013/0102082 A1*   4/2013    Majima .................. G01N 21/80
                                                          436/86

FOREIGN PATENT DOCUMENTS

CN    101055272 A        10/2007
EP    1 845 373 A1       10/2007
(Continued)

OTHER PUBLICATIONS

Office Action issued by the European Patent Office dated May 26, 2017 in corresponding EP Application No. 14164522.1-1405 which corresponds to U.S. Appl. No. 15/095,621; 5pp.
(Continued)

*Primary Examiner* — Rebecca L Martinez
(74) *Attorney, Agent, or Firm* — Studebaker & Brackett PC

(57) ABSTRACT

Provided is a measurement system for performing qualitative measurement and quantitative measurement of a measurement item of a biological sample, the measurement system including a quantitative sample adjustment criterion storage section that stores a quantitative sample adjustment criterion corresponding to a qualitative measurement result in the qualitative measurement, a determination section that determines a proper quantitative sample adjustment condition by referring to the quantitative sample adjustment criterion to determine necessity to change the quantitative sample adjustment condition based on the qualitative measurement result, and an adjustment section that adjusts the biological sample based on the quantitative sample adjustment condition determined by the determination section.

8 Claims, 19 Drawing Sheets

(51) Int. Cl.
    *G01N 33/53*    (2006.01)
    *G01N 33/487*   (2006.01)
    *G01N 33/493*   (2006.01)
    *G01N 35/00*    (2006.01)

(56) References Cited

FOREIGN PATENT DOCUMENTS

| | | |
|---|---|---|
| EP | 2 237 033 A1 | 10/2010 |
| JP | 06102272 A | 4/1994 |
| JP | 2014020802 A | 2/2014 |

OTHER PUBLICATIONS

An Office Action issued by the European Patent Office dated Oct. 19, 2017, which corresponds to EP Patent Application No. 16164522.1-1405 and is related to U.S. Appl. No. 15/095,621.

Communication pursuant to Article 94(3) EPC issued by the European Patent Office dated Jun. 14, 2018, which corresponds to European Patent Application No. 16 164 522.1-1111 and is related to U.S. Appl. No. 15/095,621.

An Office Action mailed by the State Intellectual Property Office of the People's Republic of China dated Jun. 7, 2018, which corresponds to Chinese Patent Application No. 201610210284.6 and is related to U.S. Appl. No. 15/095,621.

The extended European search report issued by the European Patent Office dated Sep. 15, 2016, which corresponds to European Patent Application No. 16164522.1-1405 and is related to U.S. Appl. No. 15/095,621.

\* cited by examiner

FIG. 5

MEASUREMENT ITEM COMPARISON TABLE T1

| URINE QUALITATIVE MEASUREMENT DEVICE M1 | URINE QUANTITATIVE MEASUREMENT DEVICE M2 |
|---|---|
| GLU | GLU |
| PRO | PRO |
| BIL | — |
| URO | — |
| CRE | CRE |
| PH | — |
| BLD | — |
| KET | — |
| NIT | — |
| LEU | — |
| ALB | ALB |
| — | AMY |
| — | NAG |
| — | BMG |
| P/C | P/C |
| A/C | A/C |

☐ : COMMON MEASUREMENT ITEM

FIG. 6

URINE QUANTITATIVE MEASUREMENT NECESSITY DETERMINATION TABLE T2

| MEASUREMENT ITEM | URINE QUALITATIVE MEASUREMENT RESULT | | | | | | |
|---|---|---|---|---|---|---|---|
| GLU | QUALITATIVE VALUE | – | ± | 1+ | 2+ | 3+ | 4+ |
| | SEMI-QUANTITATIVE VALUE (mg/dL) | – | 50 | 100 | 200 | 500 | 1000 |
| PRO | QUALITATIVE VALUE | – | ± | 1+ | 2+ | 3+ | 4+ |
| | SEMI-QUANTITATIVE VALUE (mg/dL) | – | 15 | 30 | 100 | 300 | 1000 |
| ALB | SEMI-QUANTITATIVE VALUE (mg/dL) | 10 | 30 | 80 | 150 | 300 | |
| CRE | SEMI-QUANTITATIVE VALUE (mg/dL) | 10 | 50 | 100 | 200 | 300 | |
| P/C | QUALITATIVE VALUE | DILUTE | NORMAL | 1+ | 1+ | 2+ | 2+ |
| | SEMI-QUANTITATIVE VALUE (mg/gCr) | | <80 | 200 | 400 | >500 | OVER |
| A/C | QUALITATIVE VALUE | | NORMAL | 1+ | 1+ | 2+ | |
| | SEMI-QUANTITATIVE VALUE (mg/gCr) | | <30 | 30 | 300 | >300 | OVER |

[DILUTE] : CRE 10 AND PRO –

☐ : QUANTITATIVE MEASUREMENT IS NECESSARY

FIG. 7A

MEASUREMENT RANGE COMPARISON TABLE
BETWEEN URINE QUALITATIVE MEASUREMENT DEVICE M1
AND URINE QUANTITATIVE MEASUREMENT DEVICE M2

| MEASUREMENT ITEM | URINE QUALITATIVE MEASUREMENT DEVICE M1 | URINE QUANTITATIVE MEASUREMENT DEVICE M2 |
|---|---|---|
| GLU | 0~1000 mg/dL | 2~600 mg/dL |
| PRO | 0~1000 mg/dL | 5~200 mg/dL |
| ALB | 10~300 mg/dL | 3~300 mg/dL |
| CRE | 10~300 mg/dL | 1~300 mg/dL |

FIG. 7B

URINE QUANTITATIVE MEASUREMENT ITEM CLASSIFICATION TABLE  T3

| CLASSIFICATION | MEASUREMENT ITEM |
|---|---|
| FIRST CLASSIFICATION | GLU, PRO |
| SECOND CLASSIFICATION | CRE, ALB |
| THIRD CLASSIFICATION | AMY, NAG, BMG |

FIG. 8

URINE QUANTITATIVE SAMPLE ADJUSTMENT CRITERION

| MEASUREMENT ITEM | CLASSIFICATION | URINE QUALITATIVE MEASUREMENT RESULT | QUANTITATIVE SAMPLE ADJUSTMENT CONDITION | QUANTITATIVE SAMPLE ADJUSTMENT CONDITION (SAMPLE QUANTITY (μL)) | QUANTITATIVE SAMPLE ADJUSTMENT CONDITION (DILUTION LIQUID QUANTITY (μL)) | QUANTITATIVE SAMPLE ADJUSTMENT CONDITION (LIQUID REAGENT QUANTITY (μL)) | QUANTITATIVE MEASUREMENT VALUE ARITHMETIC OPERATION PARAMETER |
|---|---|---|---|---|---|---|---|
| GLU | FIRST CLASSIFICATION | − TO 2+ | USUAL ADJUSTMENT CONDITION | 6 | 45 | 235 | 1 |
| GLU | FIRST CLASSIFICATION | NOT LESS THAN 3+ | CHANGED ADJUSTMENT CONDITION | 3 | 128 | 235 | 2.56 |
| PRO | FIRST CLASSIFICATION | − TO + | USUAL ADJUSTMENT CONDITION | 6 | 45 | 235 | 1 |
| PRO | FIRST CLASSIFICATION | NOT LESS THAN 2+ | CHANGED ADJUSTMENT CONDITION | 3 | 128 | 235 | 2.56 |
| ALB | SECOND CLASSIFICATION | 10 TO 300 mg/dL | USUAL ADJUSTMENT CONDITION | 6 | 45 | 235 | 1 |
| CRE | SECOND CLASSIFICATION | 10 TO 300 mg/dL | USUAL ADJUSTMENT CONDITION | 6 | 45 | 235 | 1 |

```
                                              8A
                                              ↓
                                                   No.00XX
      - - - - - - - - - - - - - - - - - - - - - - - - - - -
D1 ──→ ID   00000000XX              2015/03/31  12:00  ←── D2
      - - - - - - - - - - - - - - - - - - - - - - - - - - -
              D4 ─╮                    ╭─ D5
        D6      QUALITATIVE or       QUANTITATIVE
      D6 ╲    SEMI-QUANTITATIVE
  D3 ╲         D7 ─╮      D8 ╮
       GLU  ! 50 mg/dL    ! 57 mg/dL  ←──── D9
       PRO  ! 2+          ! 120 mg/dL ← *
       URO   NORMAL         —
       BIL   —              —
       CRE   100 mg/dL    D7   —    D8
       PH    7.0            —
       BLD   —              —
       KET   —              —
       NIT   —              —
       LEU   — ── D6         —
       P/C   ( 2+            —
       ALB   10 mg/dL        —
       A/C   —              —
       AMY   —              —
       NAG   —              —
       BMG   —              —
      - - - - - - - - - - - - - - - - - - - - - - - - - - -
```

FIG. 13

```
                                        No.00XX
- - - - - - - - - - - - - - - - - - - - - - - - - -
  ID    00000000XX              2015/03/31 12:00
- - - - - - - - - - - - - - - - - - - - - - - - - -
          QUALITATIVE or         QUANTITATIVE
          SEMI-QUANTITATIVE

GLU    -                        -
    PRO    -                        2 mg/dL
    URO    NORMAL                   -
    BIL    -                        -
    CRE    10 mg/dL                 8 mg/dL
    PH     7.0                      -
    BLD    -                        -
    KET    -                        -
    NIT    -                        -
    LEU    -                        -
    P/C    ! DILUTE                 ! 250 mg/gCr
    ALB    10 mg/dL                 -
    A/C    -                        -
    AMY    -                        -
    NAG    -                        -
    BMG    -                        -
```

Labels: 8B, D1 (ID), D2 (date), D3 (GLU column), D4 (QUALITATIVE or SEMI-QUANTITATIVE), D5 (QUANTITATIVE), D6, D7, D8

D4                              D5
           QUALITATIVE or              QUANTITATIVE
       D6  SEMI-QUANTITATIVE
       D6                          D7
           GLU   ! 50 mg/dL         ! 57 mg/dL
           PRO   ! 2+               ! 120 mg/dL
           URO    NORMAL              —
           BIL    -        D7         —
           CRE    100 mg/dL           —
           PH     7.0                 —
           BLD    -                   —
           KET    -                   —
           NIT    -                   —
           LEU    -       D6          —
           P/C   ! 2+                 —
           ALB    10 mg/dL            —
           A/C    -                   —
           AMY    -                   —
           NAG    -                   —
           BMG    -                   —

D10 ──→ URINE QUANTITATIVE MEASUREMENT REQUIREMENT
        AUTOMATIC DETERMINATION : GLU, PRO
D11 ──→ URINE QUANTITATIVE SAMPLE ADJUSTMENT
        CONDITION CHANGE : PRO
```

| | | No.00XX |
|---|---|---|
| D1 → ID 00000000XX | | 2015/03/31 12:00 ← D2 |

D4 — QUALITATIVE or SEMI-QUANTITATIVE    D5 — QUANTITATIVE

D3

| | | |
|---|---|---|
| GLU | - | - |
| PRO | - | - |
| URO | NORMAL | - |
| BIL | - | - |
| CRE | 200 mg/dL | - |
| PH | 7.0 | - |
| BLD | - | - |
| KET | - | - |
| NIT | - | - |
| LEU | - | - |
| P/C | NORMAL | - |
| ALB | 10 mg/dL | - |
| A/C | - | - |
| AMY | - | - |
| NAG | - | - |
| BMG | - | - |

D12 → URINE QUANTITATIVE MEASUREMENT REQUIREMENT AUTOMATIC DETERMINATION: NONE

D13 → URINE QUANTITATIVE SAMPLE ADJUSTMENT CONDITION CHANGE: NONE

FIG. 17

URINE QUANTITATIVE CALIBRATION CURVE
SELECTION CRITERION    T5

| MEASUREMENT ITEM | CLASSIFICATION | URINE QUALITATIVE MEASUREMENT RESULT | URINE QUANTITATIVE CALIBRATION CURVE |
|---|---|---|---|
| GLU | FIRST CLASSIFICATION | − TO 2+ | USUAL CALIBRATION CURVE |
| | | NOT LESS THAN 3+ | CHANGED CALIBRATION CURVE |
| PRO | FIRST CLASSIFICATION | − TO + | USUAL CALIBRATION CURVE |
| | | NOT LESS THAN 2+ | CHANGED CALIBRATION CURVE |
| CRE | SECOND CLASSIFICATION | 10 TO 300 mg/dL | USUAL CALIBRATION CURVE |
| ALB | SECOND CLASSIFICATION | 10 TO 300 mg/dL | USUAL CALIBRATION CURVE |

MEASUREMENT METHOD AND MEASUREMENT SYSTEM

BACKGROUND OF THE INVENTION

1. Field of the Invention

The present invention relates to a technique that is usable when quantitative measurement of a biological sample is performed subsequently to screening by qualitative measurement of the sample.

2. Description of the Related Art

As conventional measurement of a biological sample, Japanese Patent Application Laid-open No. H06-102272 discloses an example of a measurement device that performs urine quantitative measurement subsequently to urine qualitative measurement. Japanese Patent Application Laid-open No. H06-102272 discloses the measurement device that automatically performs urinary sediment measurement or the urine quantitative measurement based on the result of the urine qualitative measurement.

In addition, Japanese Patent Application Laid-open No. 2014-20802 describes a measurement device that automatically performs re-measurement in the case where the result of the urine quantitative measurement exceeds a measurement range. The measurement device disclosed in Japanese Patent Application Laid-open No. 2014-20802 analyzes a urine sample diluted with a predetermined dilution factor in first analysis and, in the case where the measurement result does not fall within the measurement range, the measurement device further dilutes the urine sample used in the first analysis or uses an undiluted urine sample to perform second analysis. This operation is repeated a predetermined number of times until the result of the urine quantitative measurement falls within the measurement range. According to such a measurement device, it is possible to prevent an increase in required urine sample quantity. Note that the qualitative measurement is sometimes referred to as semi-quantitative measurement.

However, the above related art has had the following problems.

That is, the measurement device of Japanese Patent Application Laid-open No. H06-102272 does not disclose measures taken in the case where, depending on the urine sample, the measurement range is exceeded in the urine quantitative measurement and accurate measurement cannot be performed. In such a case, usually, it is necessary to dilute the urine sample and perform the quantitative examination again. Accordingly, there has been a problem that it takes a long time to obtain the measurement result of the urine quantitative measurement, and an additional reagent cost is required.

In the measurement device of Japanese Patent Application Laid-open No. 2014-20802, in the case where the result of the urine quantitative measurement exceeds the measurement range, the dilution factor of the urine sample is changed based on the measurement result of the first analysis. However, there is a measurement item of which the concentration cannot be determined from the measurement result of the first analysis. In such a case, it is necessary to perform the re-measurement a plurality of times. In this case as well, there has been a problem that, due to the repetition of the measurement, it takes a long time to obtain the measurement result of the urine quantitative measurement, and the additional reagent cost is required.

In addition, in antigen-antibody reaction as an example of the urine quantitative measurement, a phenomenon (prozone phenomenon) in which a measured absorbance is small in spite of an actual high concentration of a target component to be measured so that a calculated urine quantitative measurement value is smaller than its actual value can occur. It is well known that such a phenomenon occurs not only in the antigen-antibody reaction but also in other reactions (hereafter, the phenomenon is referred to as "a prozone-like phenomenon"). Similarly to the case where the measurement range is exceeded, the measurement device described in each of Japanese Patent Application Laid-open No. H06-102272 and Japanese Patent Application Laid-open No. 2014-20802 cannot efficiently solve the problem caused by the prozone-like phenomenon in the urine quantitative measurement. As the biological sample, blood, blood plasma, and blood serum are measured in addition to urine.

SUMMARY OF THE INVENTION

The present invention has been devised in view of the above circumstances, and an object thereof is to provide a measurement method and a measurement system capable of, in the case where quantitative measurement of a measurement item of a biological sample is performed subsequently to qualitative measurement, achieving a reduction in time required for the quantitative measurement and a reduction in measurement cost.

In order to solve the above problem, the present invention adopts the following technical means.

A measurement method provided by a first aspect of the present invention is a measurement method for performing qualitative measurement and quantitative measurement of a measurement item of a biological sample, the measurement method including the steps of acquiring a qualitative measurement result of the measurement item by performing the qualitative measurement on the biological sample, determining a proper quantitative sample adjustment condition by referring to a quantitative sample adjustment criterion to determine necessity to change the quantitative sample adjustment condition based on the qualitative measurement result, adjusting the biological sample based on the quantitative sample adjustment condition determined in the step of determining the proper quantitative sample adjustment condition, and acquiring a quantitative measurement value of the measurement item by performing the quantitative measurement on the biological sample adjusted in the step of adjusting the biological sample.

Preferably, a biological sample dilution factor of the biological sample is adjusted based on the quantitative sample adjustment condition in the step of adjusting the biological sample.

Preferably, the measurement method further includes the step of determining whether or not the quantitative measurement is performed based on the qualitative measurement result acquired in the step of acquiring the qualitative measurement result.

Preferably, the measurement item is classified as a first classification that requires determination of the quantitative sample adjustment condition corresponding to the qualitative measurement result or a second classification that does not require the determination of the quantitative sample adjustment condition corresponding to the qualitative measurement result in the quantitative sample adjustment criterion.

A measurement system provided by a second aspect of the present invention is a measurement system for performing qualitative measurement and quantitative measurement of a measurement item of a biological sample, the measurement system including a quantitative sample adjustment criterion storage section that stores a quantitative sample adjustment criterion corresponding to a qualitative measurement result in the qualitative measurement, a qualitative measurement section that acquires the qualitative measurement result of the measurement item by performing the qualitative measurement on the biological sample, a determination section that determines a proper quantitative sample adjustment condition by referring to the quantitative sample adjustment criterion to determine necessity to change the quantitative sample adjustment condition based on the qualitative measurement result, an adjustment section that adjusts the biological sample based on the quantitative sample adjustment condition determined by the determination section, and a quantitative measurement section that acquires a quantitative measurement value of the measurement item by performing the quantitative measurement on the biological sample adjusted by the adjustment section.

Preferably, the quantitative sample adjustment condition is related to a sample dilution factor.

Preferably, the measurement system further includes a judgment section that judges whether or not the quantitative measurement is performed based on the qualitative measurement result acquired by the qualitative measurement section.

Preferably, the measurement item is classified as a first classification that requires determination of the quantitative sample adjustment condition corresponding to the qualitative measurement result or a second classification that does not require the determination of the quantitative sample adjustment condition corresponding to the qualitative measurement result in the quantitative sample adjustment criterion.

Preferably, the measurement item classified as the first classification has a measurement range of the quantitative measurement that is narrower than a corresponding measurement range of the qualitative measurement, and the measurement item classified as the second classification has a measurement range of the quantitative measurement that is wider than or equal to a corresponding measurement range of the qualitative measurement.

Preferably, the first classification includes a prozone-like phenomenon occurrence measurement item in which a prozone-like phenomenon occurs in the quantitative measurement.

Preferably, the prozone-like phenomenon occurrence measurement item is a protein quantity measurement.

Preferably, the measurement system further includes an arithmetic operation parameter storage section that stores an arithmetic operation parameter corresponding to the quantitative sample adjustment condition, and an arithmetic operation section that corrects the quantitative measurement value based on the arithmetic operation parameter.

Preferably, the measurement system further includes an output section that outputs an examination report in which the quantitative measurement value is described, and the output section describes quantitative sample adjustment condition change information in the examination report in a case where the determination section has changed the quantitative sample adjustment condition.

A measurement system provided by a third aspect of the present invention is a measurement system for performing qualitative measurement and quantitative measurement of a measurement item of a biological sample, the measurement system including a quantitative calibration curve selection criterion storage section that stores a quantitative calibration curve selection criterion corresponding to a qualitative measurement result, a qualitative measurement section that acquires the qualitative measurement result of the measurement item by performing the qualitative measurement on the biological sample, a determination section that determines a proper quantitative calibration curve by referring to the quantitative calibration curve selection criterion to determine necessity to change the quantitative calibration curve based on the qualitative measurement result, a quantitative measurement section that acquires a quantitative response value of the measurement item by performing the quantitative measurement on the biological sample subsequently to the qualitative measurement, and a calculation section that calculates a quantitative measurement value by applying the quantitative response value to the quantitative calibration curve.

According to the adoption of the aspect of the present invention, it is possible to provide the measurement method and the measurement system capable of, in the case where the quantitative measurement of the measurement item of the biological sample is performed subsequently to the qualitative measurement, achieving the reduction in time required for the quantitative measurement and the reduction in measurement cost.

Other features and advantages of the present invention will become more apparent from the description of embodiments made below with reference to the accompanying drawings.

BRIEF DESCRIPTION OF THE DRAWINGS

FIG. 5 is a comparison table for comparing measurement items of the urine qualitative measurement device and the urine quantitative measurement device constituting the measurement system shown in FIG. 1;

FIG. 6 is a table showing an example of a urine quantitative measurement necessity determination table of the measurement system shown in FIG. 1;

FIG. 7A is a table for explaining a relationship between a measurement range of the urine qualitative measurement device of the measurement system shown in FIG. 1 and a measurement range of the urine quantitative measurement device thereof, and FIG. 7B is a table showing an example of a urine quantitative measurement item classification table of the measurement system shown in FIG. 1;

FIG. 8 is a table showing an example of a urine quantitative sample adjustment criterion of the measurement system shown in FIG. 1;

FIG. 12 is a view showing an example of an examination report output by the measurement system shown in FIG. 1;

FIG. 13 is a view showing another example of the examination report output by the measurement system shown in FIG. 1;

FIG. 14 is a view showing another example of the examination report output by the measurement system shown in FIG. 1;

FIG. 15 is a view showing another example of the examination report output by the measurement system shown in FIG. 1;

FIG. 17 is a table showing an example of a urine quantitative calibration curve selection criterion of the measurement system shown in FIG. 16;

DESCRIPTION OF THE PREFERRED EMBODIMENTS

Hereinbelow, preferred embodiments of the present invention will be described specifically with reference to the drawings.

First Embodiment

Figure 1:
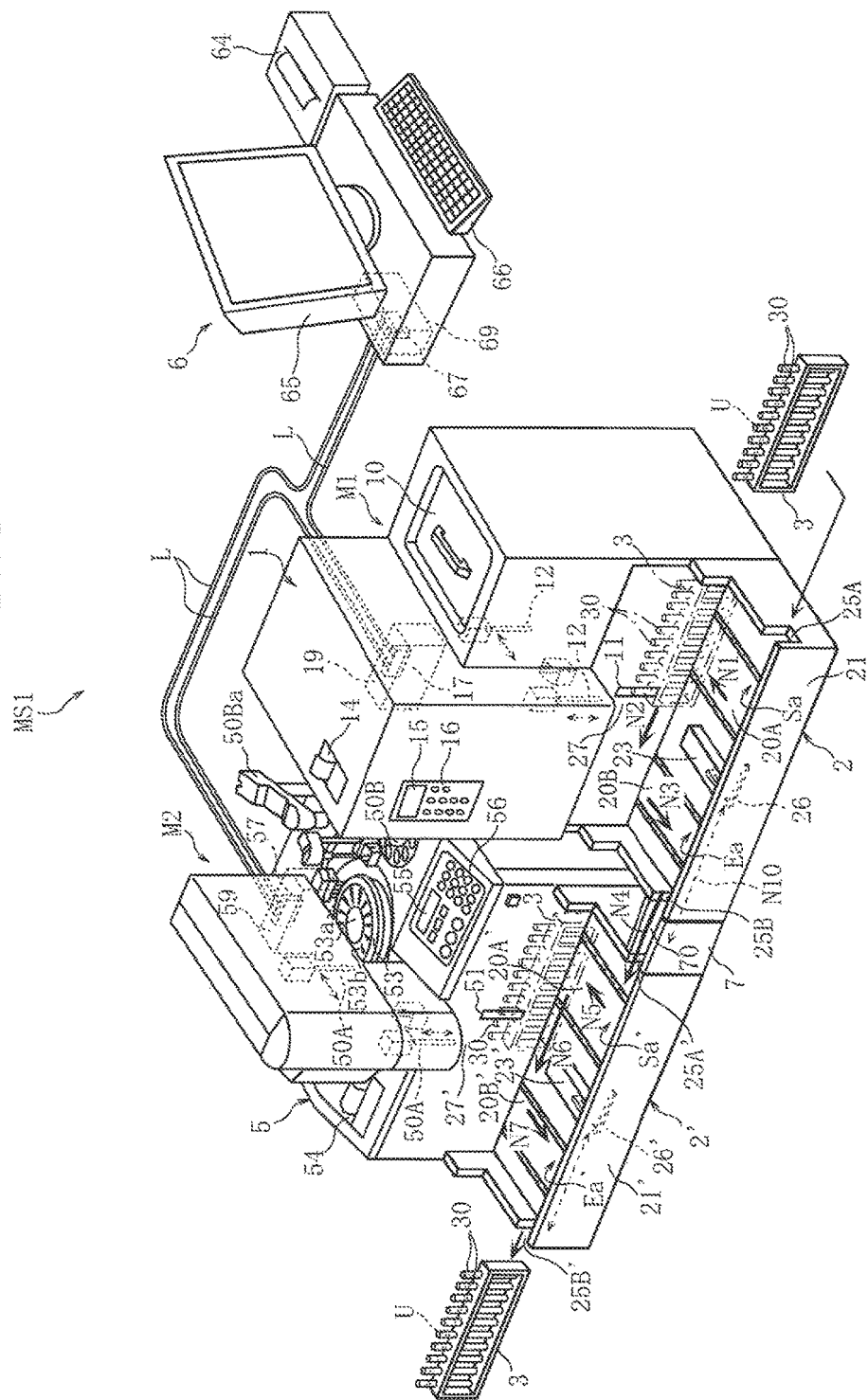
FIG. 1 is a schematic perspective view showing a measurement system according to a first embodiment of the present invention.

Each of FIGS. 1 to 4 shows an example of a measurement system to which the present invention is applied. As shown in FIG. 1, a measurement system MS1 of the present embodiment includes a urine qualitative measurement device M1, a urine quantitative measurement device M2, and an information processing device 6. The measurement system MS1 is installed in, e.g., a laboratory in a hospital, and is used to perform urine quantitative measurement subsequently to urine qualitative measurement of a measurement item of a urine sample U is performed. In the measurement system MS1, the urine qualitative measurement device M1 and the urine quantitative measurement device M2 correspond to examples of a urine qualitative measurement section and a urine quantitative measurement section respectively. In addition, the urine qualitative measurement device M1 and the urine quantitative measurement device M2 correspond to examples of a qualitative measurement section and a quantitative measurement section in the present invention. The information processing device 6 controls the operation of the entire measurement system MS1. The urine qualitative measurement device M1, the urine quantitative measurement device M2, and the information processing device 6 are directly connected to each other via communication lines L.

Note that the urine qualitative measurement device M1, the urine quantitative measurement device M2, and the information processing device 6 may be capable of data communication mutually among them appropriately, and they can be configured to be connected to each other via communication that uses a local area network (LAN) constructed in, e.g., the hospital or a line such as the Internet, or can also be configured to perform wireless communication.

The urine sample U corresponds to an example of a biological sample in the present invention. Examples of the biological sample that can be measured in the measurement system MS1 include feces, blood serum, blood plasma, and whole blood in addition to the urine sample U. With regard to the feces, a liquid obtained by filtering a suspension in which the feces are suspended is used as the sample.

Figure 2:
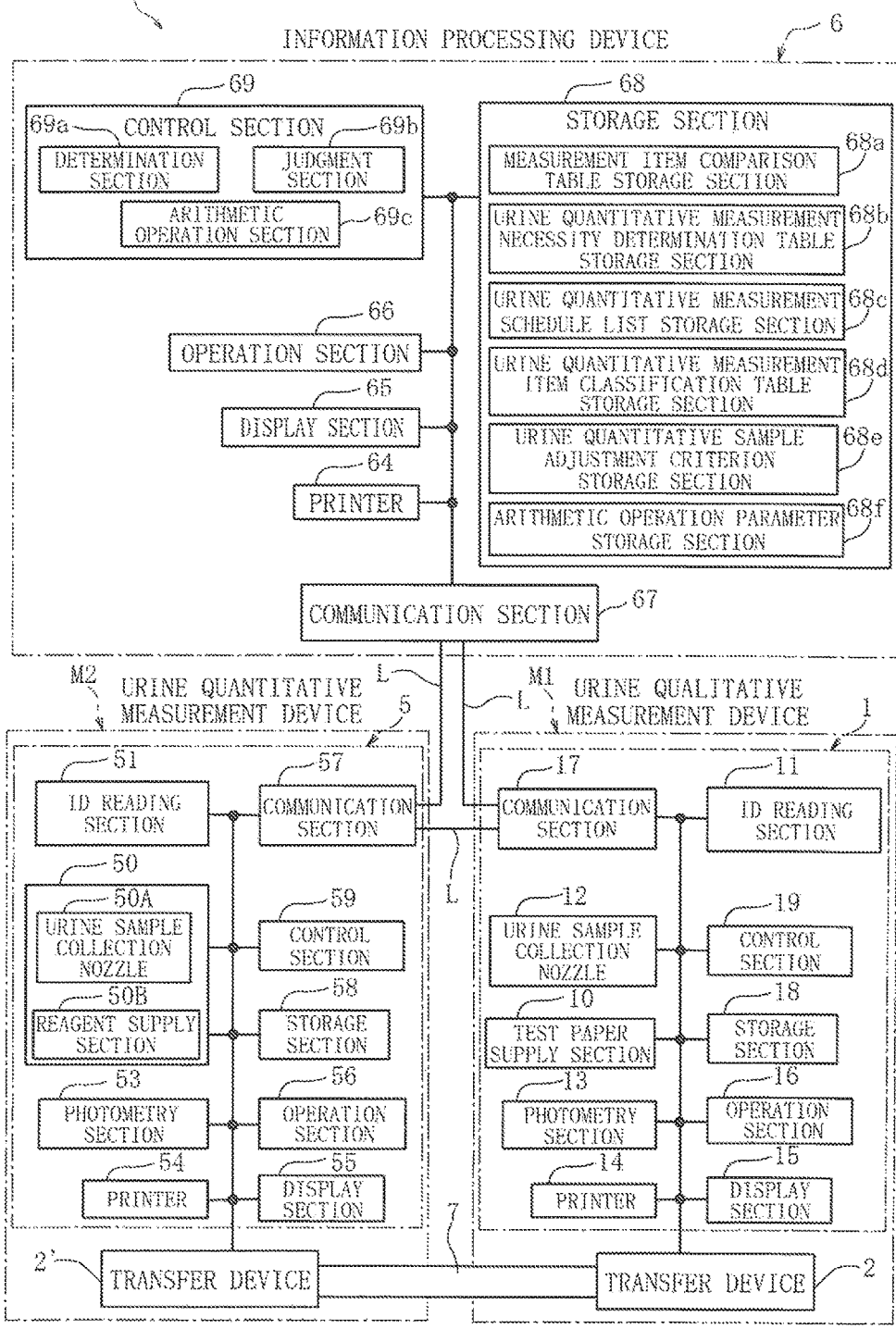
FIG. 2 is a block diagram of the measurement system shown in FIG. 1.

As shown in FIGS. 1 and 2, the urine qualitative measurement device M1 is provided for performing a qualitative measurement process of the urine sample U contained in urine sample containers 30, and has a main body portion 1 and a transfer device 2.

As shown in FIG. 1, the transfer device 2 is provided for transferring a rack 3 that holds the urine sample containers 30 upright using specific paths. The transfer device 2 has two transfer paths 20A and 20B that are separated by a partition stand 23, and a frame portion 21 that surrounds the near side and both sides of the transfer paths 20A and 20B. In the transfer device 2, when the rack 3 is placed in a start area Sa from a notched portion 25A provided in the frame portion 21, the rack 3 is transferred in directions indicated by arrows N1 to N3 sequentially, and reaches an end area Ea finally. The rack 3 having reached the end area Ea is pushed out of the transfer device 2 via a notched portion 25B by a pusher 26 that reciprocates in a direction indicated by N10. Reading of a bar code stuck to the urine sample container 30 and collection of the urine sample U from the urine sample container 30 described later are performed in the process of transferring the rack 3 in the direction indicated by the arrow N2.

As shown in FIG. 2, the main body portion 1 of the urine qualitative measurement device M1 includes a test paper supply section 10, an ID reading section 11, a urine sample collection nozzle 12, a photometry section 13, a printer 14, a display section 15, an operation section 16, a communication section 17, a storage section 18, and a control section 19.

Figure 3:
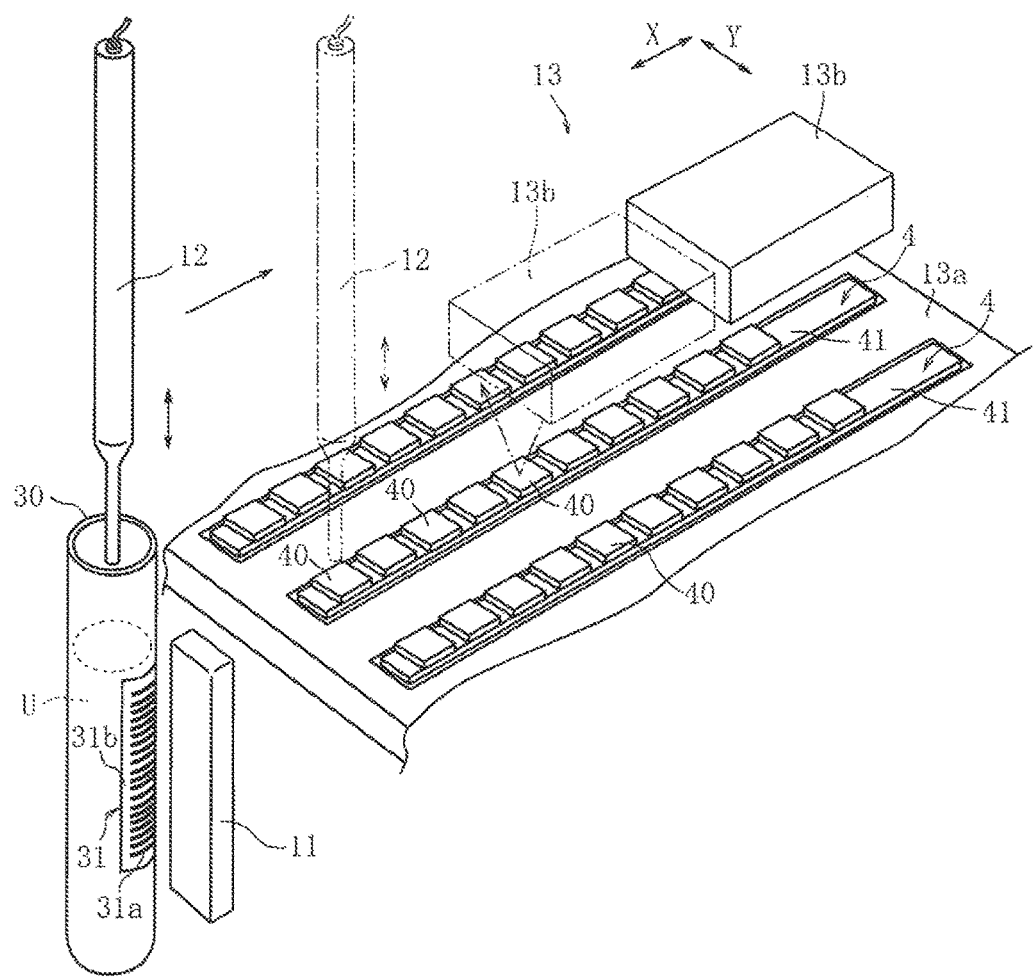
FIG. 3 is a perspective view of a principal portion showing an internal configuration of a urine qualitative measurement device constituting the measurement system shown in FIG. 1.

The urine qualitative measurement by the urine qualitative measurement device M1 is performed by using a multi-item test piece 4. The multi-item test piece 4 is preserved in a bottle (not shown). The multi-item test piece 4 is taken out of the bottle when it is used, and is put into the test paper supply section 10 shown in FIG. 1. When a measurement operation is started, as shown in FIG. 3, the multi-item test piece 4 is automatically placed on a placement stand 13a constituting the photometry section 13 described later. As shown in FIG. 3, in the multi-item test piece 4, a plurality of reagent pads 40 are disposed on a plastic stick 41.

According to the multi-item test piece 4, with a difference between the reagents contained in the individual reagent pads 40, it is possible to perform the urine qualitative measurement of a plurality of measurement items simultaneously. Examples of the measurement item that can be measured by using the multi-item test piece 4 include glucose (GLU), protein (PRO), urobilinogen (URO), bilirubin (BIL), creatinine (CRE), albumin (ALB), pH, occult blood (BLD), ketone body (KET), nitrite (NIT), leukocyte (LEU), urinary protein/creatinine ratio (P/C), and albumin/creatinine ratio (A/C). With the use of the multi-item test piece 4, it is possible to acquire qualitative values or semi-quantitative values of these measurement items. The qualitative value and the semi-quantitative value correspond to examples of a urine qualitative measurement result. In addition, the qualitative value and the semi-quantitative value correspond to examples of a qualitative measurement result in the present invention. Note that the urine qualitative measurement is described by taking the multi-item test piece 4 as an example, and the multi-item test piece 4 may also be a test piece including only one reagent pad 40.

As shown in FIG. 3, in the urine sample container 30, an information recording section 31 configured by using, e.g., a label 31*b* on which a bar code 31*a* is printed is provided. In the information recording section 31, subject identification information for identifying a subject as a provider of the urine sample U is recorded. The ID reading section 11 is, e.g., a bar code reader and, as shown in FIGS. 1 and 3, when the urine sample container 30 is transferred to the front of the ID reading section 11 by the transfer device 2, the ID reading section 11 reads the subject identification information from the information recording section 31 of the urine sample container 30. By reading the subject identification information, it is possible to confirm the ordered measurement item of the urine sample U.

The urine sample collection nozzle 12 is provided for sucking and collecting a predetermined quantity of the urine sample U from the urine sample container 30 having passed the front of the ID reading section 11 and reached a urine qualitative measurement urine collection section 27. The collected urine sample U is supplied to the photometry section 13 described later. The urine sample collection nozzle 12 performs a collection operation of the urine sample U and a dispensing operation to the reagent pad 40 with driving by a urine sample collection nozzle driving section (not shown).

As shown in FIG. 3, the photometry section 13 includes the placement stand 13*a* and an optical measuring instrument 13*b*. As described above, on the placement stand 13*a*, the multi-item test piece 4 is placed. The predetermined quantity of the urine sample U collected by the urine sample collection nozzle 12 is dispensed onto each of a plurality of the reagent pads 40 of the multi-item test piece 4. Each of the reagent pads 40 is configured to react with a predetermined component in the urine sample U and develop a color of a degree corresponding to the concentration of the component. The optical measuring instrument 13*b* is configured to be movable in X and Y directions, and capable of measuring the degree of the color development of each reagent pad 40 after the dispensing of the urine sample U as optical reflectance or the like. The qualitative value or the semi-quantitative value of the predetermined component in the urine is calculated based on measurement data acquired by the optical measuring instrument 13*b*. The measurement data such as the optical reflectance also corresponds to an example of the urine qualitative measurement result. In addition, the measurement data such as the optical reflectance also corresponds to an example of the qualitative measurement result in the present invention.

In FIGS. 1 and 2, the printer 14 is provided for associating the urine qualitative measurement result of the urine sample U with the subject identification information, printing them on a predetermined paper sheet, and outputting the paper sheet. The display section 15 includes an image display screen such as a liquid crystal display panel, and performs screen display of, e.g., the measurement result or for guiding the operation of the operation section 16. The operation section 16 is provided for an examiner to input data required for the urine qualitative measurement into the urine qualitative measurement device M1. The communication section 17 is provided for performing communication with the urine quantitative measurement device M2 and the information processing device 6 via the communication lines L. The urine qualitative measurement result acquired in the urine qualitative measurement device M1 is transmitted to the information processing device 6 or the urine quantitative measurement device M2 from the communication section 17 via the communication lines L as pair information associated with the subject identification information.

The control section 19 is configured by using, e.g., a microcomputer. The control section 19 is provided for performing control of operation processes of the individual sections of the urine qualitative measurement device M1 based on instructions from the information processing device 6. The storage section 18 stores programs and various data sets for causing the control section 19 to execute the operation control of the individual sections of the urine qualitative measurement device M1 and various data processes. In addition, the storage section 18 temporarily stores the urine qualitative measurement result acquired by, e.g., the photometry section 13.

The urine quantitative measurement device M2 is provided for performing a quantitative measurement process of a predetermined component contained in the urine sample U contained in the urine sample container 30 and, as shown in FIGS. 1 and 2, the urine quantitative measurement device M2 has a main body portion 5 and a transfer device 2'.

The transfer device 2' is for transferring the rack 3 discharged from the transfer device 2 using specific paths. As shown in FIG. 1, the transfer device 2' is connected to the transfer device 2 by using a connection member 7. In the transfer device 2', as indicated by an arrow N4, the rack 3 is pushed by the pusher 26, and is thereby moved through a transfer path 70 of the connection member 7 to a start area Sa' of a transfer path 20A' from a notched portion 25A' provided in a frame portion 21'. Thereafter, the rack 3 is transferred in directions indicated by arrows N5 to N7 sequentially, and reaches an end area Ea' of a transfer path 20B' finally. Similarly to the urine qualitative measurement device M1, the reading of the bar code of the urine sample container 30 and the collection of the urine sample U used in the urine quantitative measurement are performed in the process of transferring the rack 3 in the direction indicated by the arrow N6. The rack 3 of which the collection of the urine sample U is completed and that has reached the end area Ea' is pushed out of the transfer device 2' via a notched portion 25B' by a pusher 26'.

As shown in FIG. 2, the main body portion 5 of the urine quantitative measurement device M2 includes an adjustment section 50, an ID reading section 51, a photometry section 53, a printer 54, a display section 55, an operation section 56, a communication section 57, a storage section 58, and a control section 59. Among them, the ID reading section 51, the printer 54, the display section 55, the operation section 56, the communication section 57, the storage section 58, and the control section 59 have functions identical or similar to those of the corresponding components in the urine qualitative measurement device M1. Therefore, herein, the detailed description thereof will be omitted.

The urine measurement by the urine quantitative measurement device M2 is performed by using a liquid reagent. As described above, the urine qualitative measurement performed by the urine qualitative measurement device M1 acquires the qualitative value or the semi-quantitative value of each measurement item. In contrast to this, the urine quantitative measurement performed by the urine quantitative measurement device M2 is for performing more accurate quantitative measurement. The urine quantitative measurement device M2 can be configured to perform the quantitative measurement of, e.g., glucose (GLU), protein (PRO), creatinine (CRE), albumin (ALB), amylase (AMY), β-D-N acetylglucosaminidase (NAG), β2-microglobulin (BMG), urinary protein/creatinine ratio (P/C), and albumin/ creatinine ratio (A/C). In each measurement item, the quantitative measurement may be appropriately performed by a generally known measurement method. For example, in general, the quantitative measurement of creatinine (CRE) is performed by using Jaffe's method or an enzyme method (creatinase-sarcosine oxidase-POD method). Among these measurement items, GLU, PRO, CRE, P/C, ALB, and A/C are common to the urine quantitative measurement device M2 and the urine qualitative measurement device M1. The measurement system MS1 is configured to be capable of setting the urine quantitative measurement device M2 such that, in the case where the urine qualitative measurement device M1 cannot perform accurate measurement of these measurement items, the urine quantitative measurement device M2 automatically performs reexamination of the measurement items. It goes without saying that the examiner can order the reexamination manually, for example, by operating the information processing device 6 described later.

Figure 4:
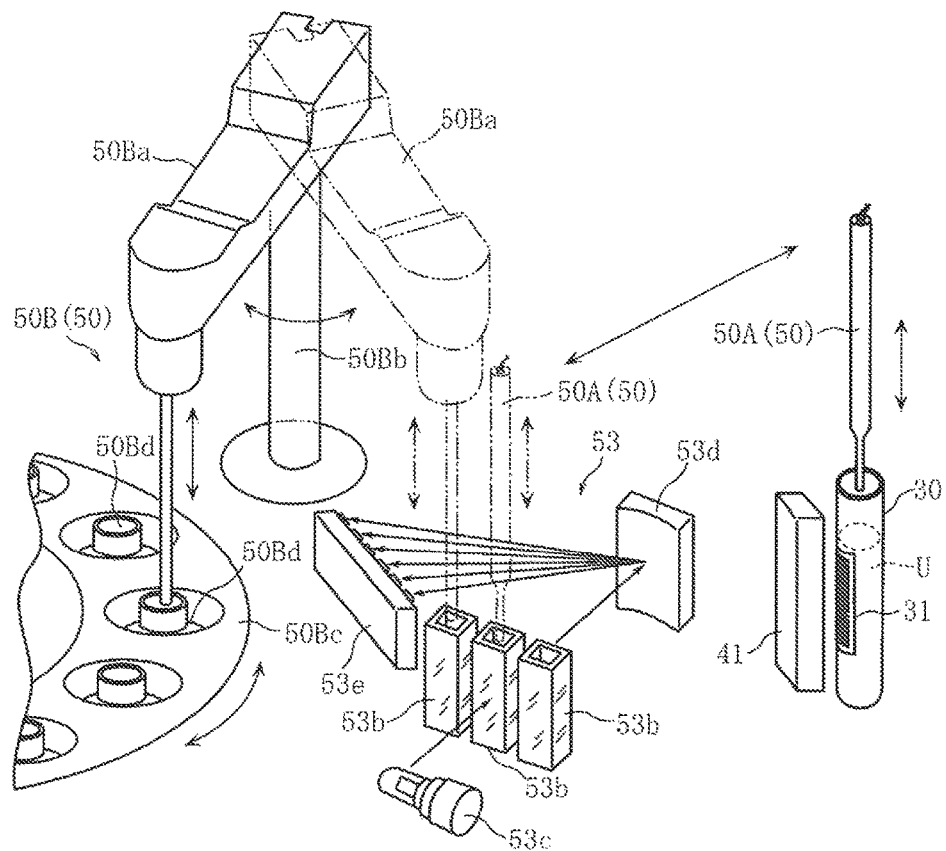
FIG. 4 is a perspective view of a principal portion showing an internal configuration of a urine quantitative measurement device constituting the measurement system shown in FIG. 1.

As shown in FIGS. 1 and 4, the photometry section 53 includes a reaction turntable 53a, reaction cells 53b, a light source lamp 53c, a concave diffraction grating 53d, and an optical receiver 53e. The reaction cells 53b are set at predetermined positions of the reaction turntable 53a.

As shown in FIGS. 2 and 4, the adjustment section 50 includes a urine sample collection nozzle 50A and a reagent supply section 50B. As shown in FIG. 4, the urine sample U collected by the urine sample collection nozzle 50A is brought to the photometry section 53 as indicated by an arrow, and is dispensed to the reaction cell 53b. The reagent supply section 50B is provided for supplying a dilution liquid and the liquid reagent to the reaction cell 53b. As shown in FIGS. 1 and 4, the reagent supply section 50B includes a reagent dispensing nozzle 50Ba and a reagent table 50Bc. On the reagent table 50Bc, bottles 50Bd filled with the dilution liquid of the urine sample U and the liquid reagent are set. A plurality of types of the liquid reagents are prepared on the reagent table 50Bc, and hence it is possible to perform the measurement of a plurality of the measurement items on one urine sample U. The reagent dispensing nozzle 50Ba moves between the reagent table 50Bc and the reaction turntable 53a by rotating about a support 50Bb and dispenses the dilution liquid and the liquid reagent to the reaction cell 53b. A liquid mixture of the urine sample U, the dilution liquid, and the liquid reagent in the reaction cell 53b serves as a reaction liquid for the measurement.

The dispensing quantity of the urine sample U to the reaction cell 53b is configured to be changeable. In addition, the dispensing quantity of the dilution liquid or the liquid reagent to the reaction cell 53b is also configured to be changeable. By changing at least one of the dispensing quantities of the urine sample U, the dilution liquid, and the liquid reagent, it is possible to change the dilution factor of the urine sample U in the reaction liquid. By changing the dilution factor, it is possible to change a measurement range of the measurement item as a target. The change of the dilution factor of the urine sample U can be a urine quantitative sample adjustment condition described later.

The liquid reagent is configured to react with a predetermined component contained in the urine sample U, and develop a color of a degree corresponding to the concentration of the component. As shown in FIG. 4, light emitted from the light source lamp 53c passes through the reaction cell 53b as indicated by an arrow, is separated by the concave diffraction grating 53d, and is detected by the optical receiver 53e as absorbance. A quantitative measurement concentration of the predetermined component in the urine is calculated based on the absorbance. The absorbance corresponds to an example of a urine quantitative measurement value. In addition, the absorbance corresponds to an example of a quantitative measurement value in the present invention. The quantitative measurement concentration of the predetermined component in the urine sample U also corresponds to an example of the urine quantitative measurement value. Further, the quantitative measurement concentration of the predetermined component in the urine sample U also corresponds to an example of the quantitative measurement value in the present invention. Note that the absorbance or the quantitative measurement concentration obtained by the measurement by the photometry section 53 is temporarily stored in the storage section 58 until being transmitted to the information processing device 6.

The information processing device 6 is provided for controlling the operation of the entire measurement system MS1, and is configured by using, e.g., a personal computer. As shown in FIG. 2, the information processing device 6 includes a printer 64, a display section 65, an operation section 66, a communication section 67, a storage section 68, and a control section 69.

The printer 64 is provided for associating the urine qualitative measurement value and the urine quantitative measurement value of the urine sample U with the subject identification information, printing them on a predetermined paper sheet as an examination report, and outputting the paper sheet, and corresponds to an example of an output section in the present invention. The printer 64 is capable of outputting information on the urine quantitative sample adjustment condition. The display section 65 includes an image display screen such as a liquid crystal display panel, and performs screen display for, e.g., guiding the operation of the operation section 66. The display section 65 may also be caused to display the measurement value of each measurement item of the urine sample U. In this case, it follows that the display section 65 also corresponds to a specific example of the output section in the present invention. The operation section 66 is provided for inputting the subject identification information, the measurement item of each urine sample U, the urine quantitative sample adjustment condition, a urine quantitative measurement value arithmetic operation parameter, and a calibration curve of each measurement item to the information processing device 6 according to an operation guide displayed on the display section 65.

The control section 69 is configured by using, e.g., a microcomputer and, as shown in FIG. 2 in particular, the control section 69 includes a determination section 69a, a judgment section 69b, and an arithmetic operation section 69c. In the urine qualitative measurement device M1 and the urine quantitative measurement device M2, the control section 19 and the control section 59 are provided respectively, and the control sections 19 and 59 are also controlled by the control section 69 of the information processing device 6.

The determination section 69a is a section that determines the urine quantitative sample adjustment condition by referring to a urine quantitative sample adjustment criterion T4 stored in a urine quantitative sample adjustment criterion storage section 68e described later based on the urine qualitative measurement result acquired by the urine qualitative measurement device M1. The judgment section 69b judges whether or not the urine quantitative measurement by the urine quantitative measurement device M2 is performed based on the urine qualitative measurement result acquired by the urine qualitative measurement device M1. When the judgment section 69b performs this judgment, the judgment section 69b refers to a measurement item comparison table T1 and a urine quantitative measurement necessity determination table T2. The arithmetic operation section 69c corrects the absorbance or the quantitative measurement concentration acquired by the urine quantitative measurement device M2 based on an arithmetic operation parameter stored in an arithmetic operation parameter storage section 68f.

In addition, the control section 69 performs control of the operation processes of the urine qualitative measurement device M1 and the urine quantitative measurement device M2, management of the urine qualitative measurement result acquired by the urine qualitative measurement device M1, and management of output of the urine qualitative measurement result and the urine quantitative measurement value.

The storage section 68 is configured by using, e.g., a memory, an HDD, or an SSD and, as shown in FIG. 2 in particular, the storage section 68 includes a measurement item comparison table storage section 68a, a urine quantitative measurement necessity determination table storage section 68b, a urine quantitative measurement schedule list storage section 68c, a urine quantitative measurement item classification table storage section 68d, the urine quantitative sample adjustment criterion storage section 68e, and the arithmetic operation parameter storage section 68f. The urine quantitative measurement item classification table storage section 68d is an example of a urine quantitative measurement item classification storage section. In addition, the storage section 68 stores programs and various data sets for causing the control section 69 to execute the operation control of the individual sections of the measurement system MS1 and various data processes. For example, the storage section 68 stores the calibration curve, the urine qualitative measurement result, and the urine quantitative measurement result of each measurement item.

FIG. 5 shows an example of the measurement item comparison table stored in the measurement item comparison table storage section 68a. The measurement item comparison table T1 has a section of the measurement item of the urine qualitative measurement device M1 and a section of the measurement item of the urine quantitative measurement device M2. As described above, examples of the measurement item of the urine qualitative measurement device M1 include GLU, PRO, BIL, URO, CRE, PH, BLD, KET, NIT, LEU, ALB, P/C, and A/C. On the other hand, examples of the measurement item of the urine quantitative measurement device M2 include GLU, PRO, CRE, ALB, AMY, NAG, BMG, P/C, and A/C. As is apparent from FIG. 5, the measurement items common to both of them are GLU, PRO, CRE, P/C, ALB, and A/C. In the case where the item of the urine qualitative measurement is one of these six items, the judgment section 69b recognizes that the judgment of whether or not the urine quantitative measurement is necessary can be performed on the measurement item based on the urine qualitative measurement result. Note that, in these six items, the measurement principle of the urine qualitative measurement and the measurement principle of the urine quantitative measurement do not need to be identical to each other.

FIG. 6 shows an example of the urine quantitative measurement necessity determination table stored in the urine quantitative measurement necessity determination table storage section 68b. The urine quantitative measurement necessity determination table T2 shown in FIG. 6 shows a threshold value of the urine quantitative measurement necessity determination. In the case where the urine qualitative measurement result has a level indicated by a part surrounded by a thick line in the urine quantitative measurement necessity determination table T2, the judgment section 69b judges that the urine quantitative measurement is necessary. For example, when attention is paid to PRO, the threshold value is present between the qualitative value − and the qualitative value ±. That is, the judgment section 69b automatically judges that the urine quantitative measurement is necessary on the condition that the level of the urine qualitative measurement result is not less than the qualitative value ±(the semi-quantitative value 15). In contrast to this, in the case where the level of the urine qualitative measurement result is the qualitative value −, the judgment section 69b automatically judges that the urine quantitative measurement is not necessary. The judgment section 69b performs the judgment on GLU, ALB, and A/C similarly. In the case where the measurement item is P/C, the judgment section 69b judges that the urine quantitative measurement is necessary on the condition that the qualitative value is "DILUTE". In this case, the information processing device 6 causes the urine quantitative measurement device M2 to perform the quantitative measurement of PRO and CRE. Otherwise, the judgment section 69b judges that the urine quantitative measurement is not necessary.

FIG. 7A shows a table in which the measurement range of the urine qualitative measurement device M1 and the measurement range of the urine quantitative measurement device M2 are compared with each other with regard to GLU, PRO, ALB, and CRE.

As is apparent from FIG. 7A, with regard to GLU and PRO, the measurement range of the urine quantitative measurement is narrower than the measurement range of the urine qualitative measurement. Accordingly, with regard to GLU and PRO, in the case where the measurement result higher than the measurement range of the urine quantitative measurement device M2 is exhibited at the stage of the urine qualitative measurement by the urine qualitative measurement device M1, there is a high possibility that the accurate urine quantitative measurement cannot be performed in a high-concentration area.

Further, with regard to PRO, the quantitative measurement is performed by using a phenomenon in which, when red bromopyrogallol red-indium complex combines with protein under an acid condition, the maximum absorption wave length shifts to the side of a long wave length and the color is changed to purple. It is well known that, in the case where the quantitative measurement is performed by using this measurement principle, a prozone-like phenomenon can occur. In the case where the quantitative measurement of a high-concentration sample is performed under the condition that the prozone-like phenomenon can occur, a problem arises in that the quantitative measurement result is not displayed as an abnormal value.

Therefore, in the case where the measurement item is GLU or PRO, it is preferable to take measures by referring to the result of the urine qualitative measurement before the urine quantitative measurement is performed.

In contrast to this, as shown in FIG. 7A, with regard to ALB and CRE, the measurement range of the urine quantitative measurement is wider than or equal to the measurement range of the urine qualitative measurement. Consequently, in the case where the measurement item is ALB or CRE, there is a high possibility that the accurate quantitative measurement result can be acquired even without taking special measures before the urine quantitative measurement is performed.

Based on the foregoing, the measurement item of the urine quantitative measurement device M2 can be classified as in a urine quantitative measurement item classification table T3 shown in FIG. 7B. That is, the measurement item that is measured also in the urine qualitative measurement device M1 and has the measurement range narrower than that of the urine qualitative measurement is classified as a first classification. Specifically, GLU and PRO are classified as the first classification. The measurement item that is measured also in the urine qualitative measurement device M1 and has the measurement range wider than or equal to that of the urine qualitative measurement is classified as a second classification. Specifically, ALB and CRE are classified as the second classification. In addition, the measurement item that is not measured in the urine qualitative measurement device M1 is classified as a third classification. Specifically, AMY, NAG, and BMG are classified as the third classification.

From the foregoing, with regard to the measurement item classified as the first classification, the determination section 69a determines whether or not the urine quantitative sample adjustment condition is changed in accordance with the level of the urine qualitative measurement result performed in the urine qualitative measurement device M1. FIG. 8 shows an example of the urine quantitative sample adjustment criterion stored in the urine quantitative sample adjustment criterion storage section 68e. The urine quantitative sample adjustment criterion T4 describes a criterion of determination of whether or not the urine quantitative sample adjustment condition is changed. The urine quantitative sample adjustment criterion storage section 68e corresponds to an example of a quantitative sample adjustment criterion storage section in the present invention. The urine quantitative sample adjustment criterion T4 corresponds to an example of a quantitative sample adjustment criterion in the present invention. In addition, the urine quantitative sample adjustment condition corresponds to an example of a quantitative sample adjustment condition in the present invention.

The urine quantitative sample adjustment criterion T4 shows a threshold value of a urine quantitative sample adjustment condition change necessity determination. For example, when attention is paid to PRO, the threshold value is present between the qualitative value + and the qualitative value 2+. That is, the determination section 69a automatically determines that the change of the urine quantitative sample adjustment condition is necessary on the condition that the level of the urine quantitative measurement result is not less than the qualitative value 2+(the semi-quantitative value 100). In contrast to this, in the case where the level of the urine qualitative measurement result is not more than the qualitative value 1+(the semi-quantitative value 30), the determination section 69a automatically determines that the change of the urine quantitative sample adjustment condition is not necessary. The determination section 69a determines the necessity of the urine quantitative sample adjustment condition change on GLU similarly.

In addition, the urine quantitative sample adjustment criterion T4 describes the urine quantitative sample adjustment condition. The urine quantitative sample adjustment condition includes a usual adjustment condition that is usually used and a changed adjustment condition that is obtained by changing the usual adjustment condition. The usual adjustment condition is a urine quantitative sample adjustment condition that is set as a default condition. The determination section 69a selects the changed adjustment condition in the case where the determination section 69a determines that the urine quantitative sample adjustment condition is to be changed, and selects the usual adjustment condition in the case where the determination section 69a determines that the urine quantitative sample adjustment condition is not to be changed.

As shown in FIG. 8, in GLU, the changed adjustment condition applied in the case where the urine qualitative measurement result is not less than 3+ has a smaller sample quantity and a larger dilution liquid quantity than those in the usual adjustment condition. In addition, in PRO, similarly to the case of GLU, the changed adjustment condition applied in the case where the urine qualitative measurement result is not less than 2+ has a smaller sample quantity and a larger dilution liquid quantity than those in the usual adjustment condition. These changed adjustment conditions are conditions that increase the dilution factor of the urine sample U to increase the measurement range as compared with the usual adjustment condition.

On the other hand, in the case where the urine qualitative measurement result is from − to 2+ in GLU and in the case where the urine qualitative measurement result is from − to 1+ in PRO, even when the sample adjustment is performed with the usual adjustment condition, it is predicted that the quantitative measurement is normally completed. Therefore, in these cases, the determination section 69a selects the usual adjustment condition, and determines that the sample adjustment is performed with this condition.

An example of the urine quantitative sample adjustment condition includes the dilution factor of the urine sample. At least one of the quantitative sample adjustment condition urine sample quantity, the dilution liquid quantity, and the liquid reagent quantity is adjusted and they are combined, whereby the dilution factor of the urine sample is set.

Note that the number of kinds of the changed adjustment condition does not need to be one. A plurality of changed adjustment conditions may be prepared and a proper changed adjustment condition may be selected from them.

With regard to CRE and ALB classified as the second classification, it is not necessary to change the urine quantitative sample adjustment condition. Accordingly, the urine quantitative sample adjustment criterion T4 describes only the usual adjustment condition. The determination section 69a does not select the urine quantitative sample adjustment condition, and determines that the sample adjustment is performed with the usual adjustment condition.

In addition, with regard to the measurement items AMY, NAG, and BMG classified as the third classification, it is not necessary to change the urine quantitative sample adjustment condition. The urine quantitative sample adjustment criterion T4 describes only the usual adjustment condition (not shown). Therefore, in the case where the measurement item belongs to this classification, the determination section 69a does not select the urine quantitative sample adjustment condition, and determines that the sample adjustment is performed with the usual adjustment condition.

The arithmetic operation parameter storage section 68f is a section that stores the arithmetic operation parameter. The arithmetic operation parameter constitutes part of the urine quantitative sample adjustment criterion T4. In the case where the urine sample U is adjusted with the changed adjustment condition, the arithmetic operation section 69c corrects the urine quantitative measurement value such that the urine quantitative measurement value becomes equal to that in the case where the urine sample U is adjusted with the usual adjustment condition.

The urine quantitative measurement schedule list storage section 68c is a section, in the storage section 68, which stores a urine quantitative measurement schedule list (not shown). In the case where the judgment section 69b judges that the urine quantitative measurement is necessary based on the result of the urine qualitative measurement, the subject identification information and the measurement item corresponding to the urine sample U of which the urine qualitative measurement has been performed are automatically added to the urine quantitative measurement schedule list. The urine quantitative measurement device M2 executes the urine quantitative measurement in accordance with the urine quantitative measurement schedule list.

The communication sections 17, 57, and 67 are connected to each other via the communication lines L, and perform data exchange among the urine qualitative measurement device M1, the urine quantitative measurement device M2, and the information processing device 6.

Next, a description will be given of an example of operation process procedures of the measurement system MS1 by the control section 69 of the information processing device 6 with reference to flowcharts shown in FIGS. 9 to 11 and FIGS. 1 to 8.

Figure 9:
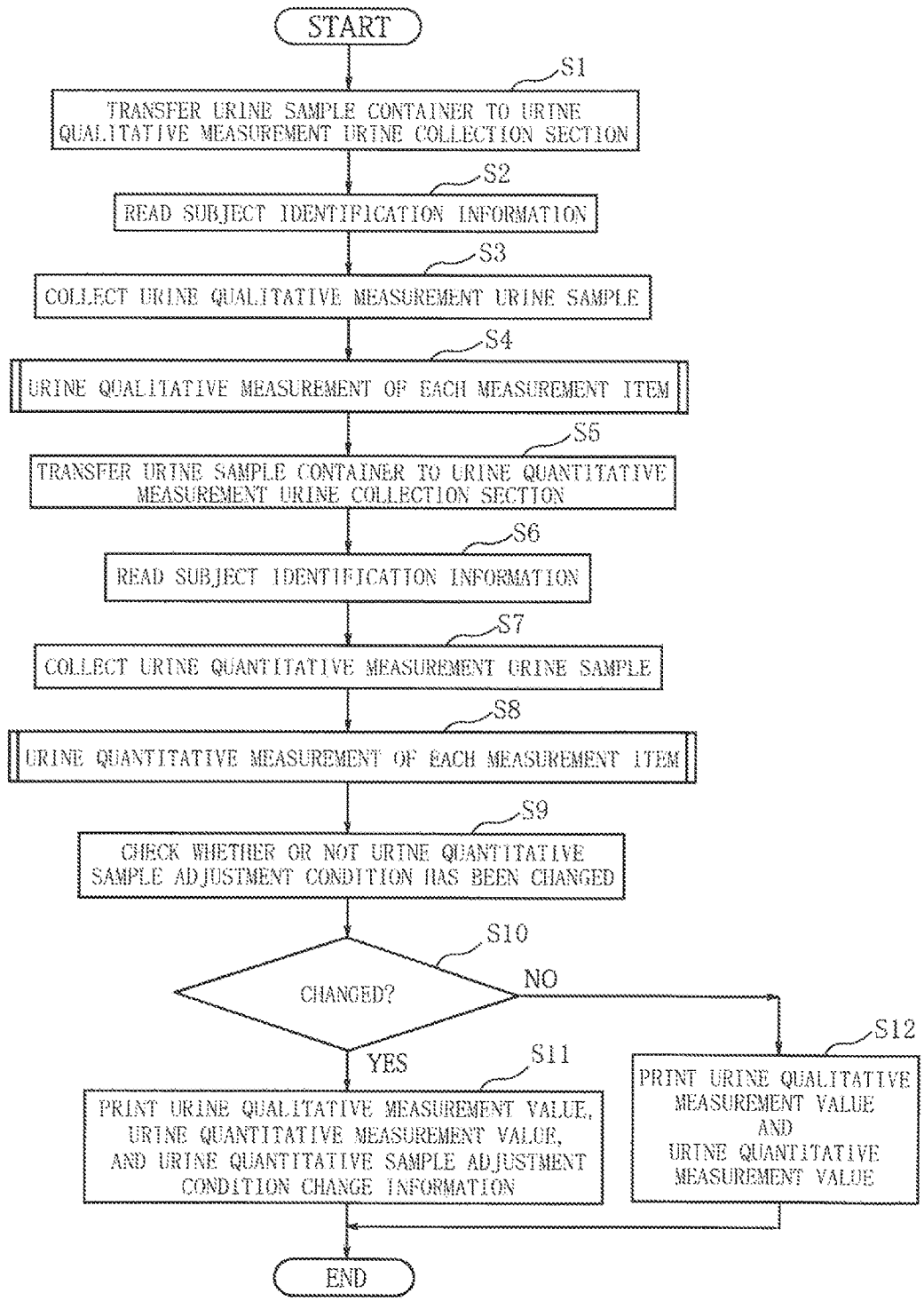
FIG. 9 is a flowchart showing an example of operation process procedures of a control section of the measurement system shown in FIG. 1.

As shown in the flowchart in FIG. 9, when the rack 3 that holds the urine sample container 30 in which the urine sample U is contained is put into the transfer device 2, the rack 3 is transferred to the urine qualitative measurement urine collection section 27 that is positioned midway in the transfer path indicated by the arrow N2 (S1). While the rack 3 is transferred to the urine qualitative measurement urine collection section 27, the bar code 31a of the urine sample container 30 is read by the ID reading section 11 (S2). In the urine qualitative measurement urine collection section 27, the urine sample collection nozzle 12 collects the urine sample U (S3). Data of the bar code 31a includes the subject identification information, and the control section 69 refers to the ordered measurement item of the urine sample U by using the subject identification information, and causes the urine qualitative measurement device M1 to perform the urine qualitative measurement of each measurement item (S4). The urine qualitative measurement of each measurement item is performed in accordance with a subroutine shown in FIG. 10.

Figure 10:
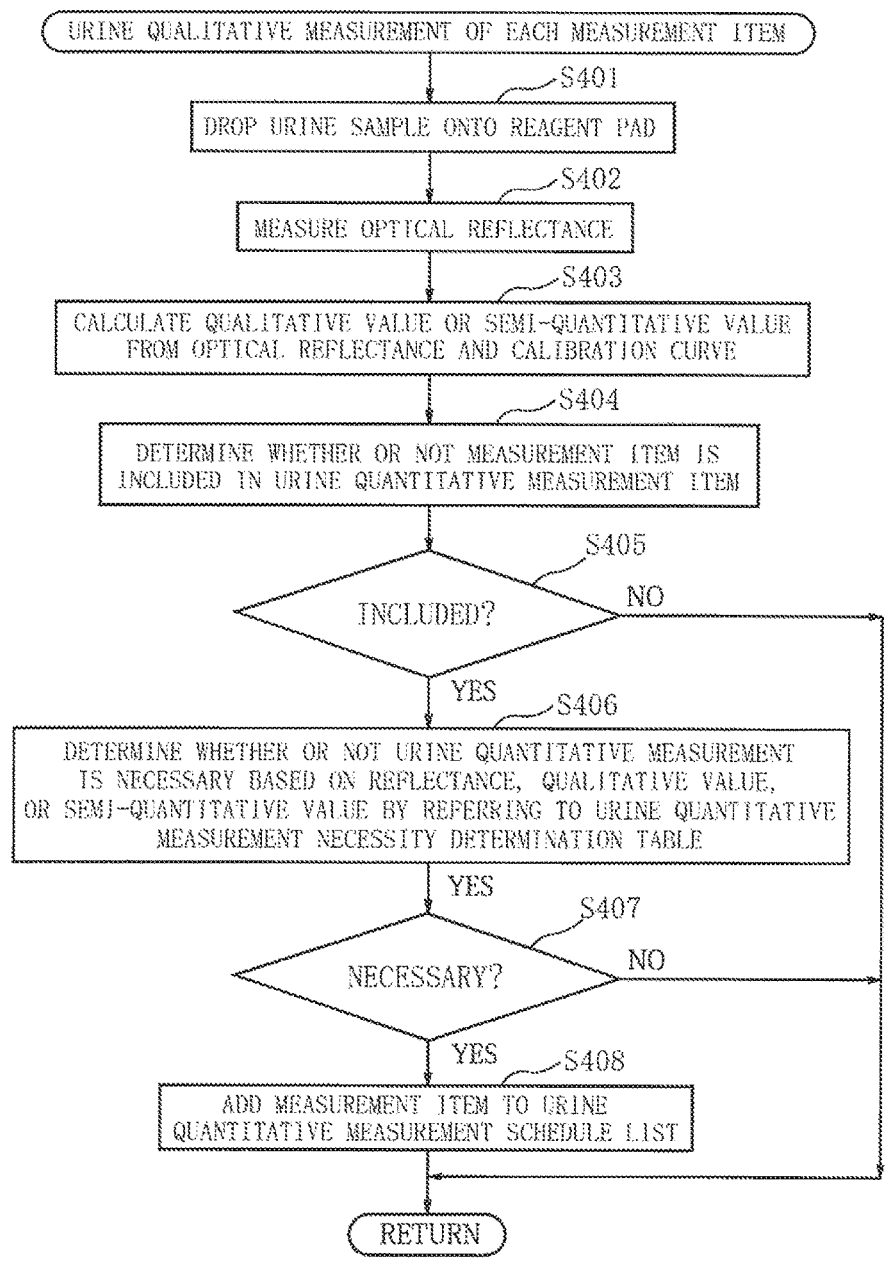
FIG. 10 is a flowchart showing an example of a urine qualitative measurement subroutine of each measurement item in the flowchart shown in FIG. 9.

As shown in the flowchart in FIG. 10, the urine sample collection nozzle 12 drops the urine sample U onto the reagent pad 40 (S401). The optical measuring instrument 13b measures the color developed on the reagent pad 40 in accordance with the quantity of the predetermined component contained in the urine sample U, and measures the optical reflectance (S402). The control section 69 applies the optical reflectance to the calibration curve stored in the storage section 68, and calculates the qualitative value or the semi-quantitative value (S403).

Next, the judgment section 69b determines whether or not the measurement item that is currently measured is included in the measurement item of the urine quantitative measurement device M2 (S404). The judgment section 69b refers to the measurement item comparison table T1 shown in FIG. 5 and, in the case where the measurement item is GLU, PRO, CRE, ALB, P/C, or A/C, the judgment section 69b judges that the measurement item is included therein (S405: YES).

Next, the judgment section 69b refers to the urine quantitative measurement necessity determination table T2 shown in FIG. 6, and judges whether or not the urine quantitative measurement is necessary (S406). In this case, as described above, in the case where the judgment section 69b judges that the urine quantitative measurement is necessary, the measurement item is automatically added to the urine quantitative measurement schedule list (S407: YES, S408).

In contrast to this, in the case where the judgment section 69b judges that the measurement item that is currently measured is not included in the measurement item of the urine quantitative measurement device M2, the procedures return to the flowchart in FIG. 9 (S405: NO). In the case where the judgment section 69b judges that the urine quantitative measurement of the measurement item that is currently measured is not necessary, the procedures return to the flowchart in FIG. 9 (S407: NO).

When the urine qualitative measurement by the urine qualitative measurement device M1 is completed, the rack 3 is transferred from the transfer device 2 to the transfer device 2' via the connection member 7. In the transfer device 2', similarly to the case of the transfer device 2, the rack 3 is transferred to a urine quantitative measurement urine collection section 27' that is positioned midway in the transfer path indicated by the arrow N6 (S5). At this point, as shown in the flowchart in FIG. 9, the reading of the subject identification information is performed by the ID reading section 51 (S6), and the urine sample U used in the urine quantitative measurement is collected by the urine sample collection nozzle 50A (S7). Next, the control section 69 refers to the urine quantitative measurement schedule list based on the subject identification information, and causes the urine quantitative measurement device M2 to perform the required urine quantitative measurement (S8). The urine quantitative measurement of each measurement item is performed in accordance with a subroutine shown in FIG. 11.

Figure 11:
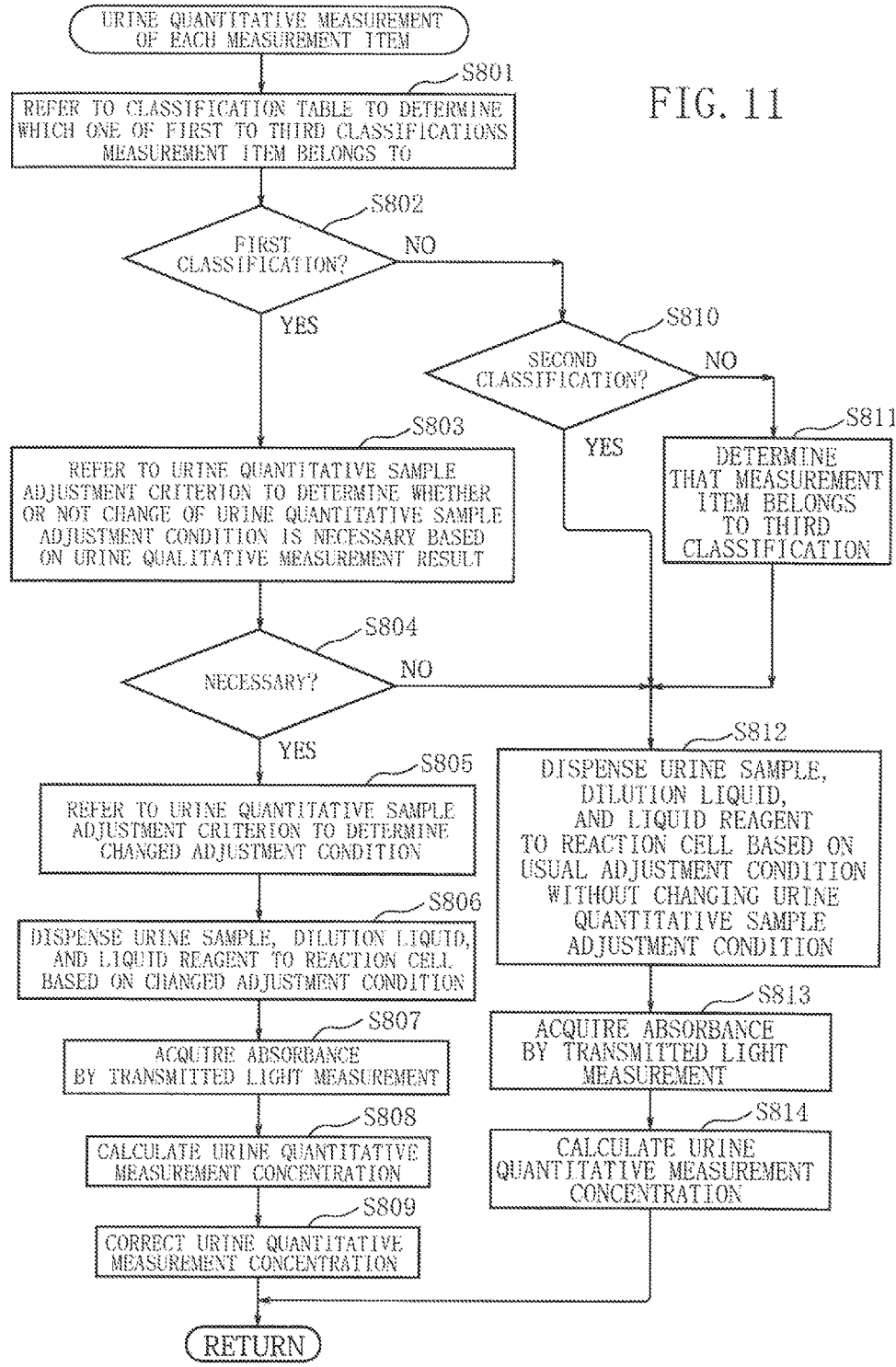
FIG. 11 is a flowchart showing an example of a urine quantitative measurement subroutine of each measurement item in the flowchart shown in FIG. 9.

In the flowchart shown in FIG. 11, the determination section 69a refers to the urine quantitative measurement item classification table T3 shown in FIG. 7B, and determines which one of the first to third classifications the measurement item is classified as (S801). For example, the measurement items GLU and PRO are classified as the first classification. In the case the measurement item is classified as the first classification, the determination section 69a refers to the urine quantitative sample adjustment criterion T4 shown in FIG. 8, and determines whether or not the change of the urine quantitative sample adjustment condition is necessary (S802: YES, S803). For example, in the case where the qualitative value of the measurement item GLU is not less than 3+(the semi-quantitative value 500), the determination section 69a determines that the urine quantitative sample adjustment condition is to be changed (S804: YES). In the case where the qualitative value of the measurement item PRO is not less than 2+(the semi-quantitative value 100), the determination section 69a determines that the urine quantitative sample adjustment condition is to be changed (S804: YES).

Next, the determination section 69a refers to the urine quantitative sample adjustment criterion T4 shown in FIG. 8, and determines that the changed adjustment condition is selected from the usual adjustment condition and the changed adjustment condition (S805). For example, in the case where the measurement item is GLU, the urine sample collection nozzle 50A reduces the quantity of the urine sample U from 6 μL to 3 μL based on the changed adjustment condition, and dispenses the urine sample U to the reaction cell 53b. In addition, the reagent dispensing nozzle 50Ba increases the quantity of the dilution liquid from 45 μL to 128 μL, and dispenses the dilution liquid to the reaction cell 53b. The reagent dispensing nozzle 50Ba dispenses the liquid reagent to the reaction cell 53b without changing the quantity of the liquid reagent. In the case where the measurement item is PRO as well, the dispensing of the urine sample U, the dilution liquid, and the liquid reagent is performed similarly (S806).

In the reaction cell 53b, the liquid reagent reacts with the predetermined component contained in the urine sample U to develop a color of a degree corresponding to the concentration of the component. The photometry section 53 detects the developed color as the absorbance (S807). The arithmetic operation section 69c applies the absorbance to the calibration curve to thereby calculate the urine quantitative measurement concentration of the predetermined component in the urine (S808). In addition, the arithmetic operation section 69c corrects the urine quantitative measurement concentration based on the arithmetic operation parameter described in the urine quantitative sample adjustment criterion T4 (S809).

In the case where the determination section 69a determines that the measurement item does not belong to the first classification (S802: NO), and determines that the measurement item belongs to the second classification (S801: YES), or in the case where the determination section 69a determines that the measurement item does not belong to the second classification (S810: NO), and determines that the measurement item belongs to the third classification (S811), the determination section 69a refers to the urine quantitative sample adjustment criterion T4 shown in FIG. 8, and determines that the usual adjustment condition is selected (S812). That is, in the case where the measurement item is CRE that belongs to the second classification, the urine sample collection nozzle 50A dispenses 6 µL of the urine sample U to the reaction cell 53b based on the usual adjustment condition. In addition, the reagent dispensing nozzle 50Ba dispenses 45 µL of the dilution liquid to the reaction cell 53b. The dispensing quantity of the liquid reagent is not changed, and 235 µL of the liquid reagent is dispensed. The determination section 69a performs the same determination on ALB.

In the case where the measurement item belongs to the third classification as well, the same measures are taken (S812).

In addition, even in the case where the measurement item belongs to the first classification, in the case where the determination section 69a determines that it is not necessary to change the urine quantitative sample adjustment condition, the same measures are taken (S804: NO, S812).

The photometry section 53 detects the color developed in the reaction cell 53b as the absorbance (S813). The arithmetic operation section 69c applies the absorbance to the calibration curve to thereby calculate the concentration of the predetermined component in the urine (S814). At the point of time when this process is completed, the procedures return to the flowchart shown in FIG. 9.

Note that, in the above example, the necessity to change the urine quantitative sample adjustment condition is determined when the measurement item belongs to the first classification, but the necessity to change the urine quantitative sample adjustment condition is not determined when the measurement item belongs to the second or third classification. However, even when the measurement item belongs to the second or third classification, the determination of the necessity to change the urine quantitative sample adjustment condition may be performed, the determination criterion that differs from one classification to another may be used, and the sample adjustment condition change that differs from one classification to another may be performed. In addition, the measurement item in which the necessity to change the urine quantitative sample adjustment condition is not determined may be collectively classified as the second classification.

Next, in the flowchart shown in FIG. 9, the control section 69 checks whether or not the urine quantitative sample adjustment condition has been changed in the urine quantitative measurement (S9). In the case where the control section 69 determines that the urine quantitative sample adjustment condition has been changed, the control section 69 causes the printer 64 to print the urine qualitative measurement value, the urine quantitative measurement value, and urine quantitative sample adjustment condition change information on a predetermined examination report in association with the subject identification information, and output the examination report (S10: YES, S11). Note that, as the urine quantitative sample adjustment condition change information, the changed condition may be output, and a mark indicative of the change of the adjustment condition may also be output. On the other hand, in the case where the urine quantitative sample adjustment condition is not changed, the urine qualitative measurement value and the urine quantitative measurement value are printed (S10: NO, S12). In this case, the urine quantitative sample adjustment condition change information is not printed. Alternatively, information indicating that the urine quantitative sample adjustment condition is not changed or a mark indicating that the urine quantitative sample adjustment condition is not changed may be positively printed.

FIG. 12 shows an example of the examination report output by the printer 64. An examination report 8A includes a subject identification information description part D1, a date description part D2, a measurement item description section D3, a urine qualitative measurement value description section D4, and a urine quantitative measurement value description section D5. In the examination report 8A, the urine qualitative measurement value and the urine quantitative measurement value are output simultaneously. Note that the urine qualitative measurement value is described as the qualitative value or the semi-quantitative value. In the case where the measurement value is an abnormal value, a sign "!" D6 or D7 is added. In the case where the urine quantitative measurement is caused to be automatically performed from the result of the urine qualitative measurement value by the judgment section 69b, a sign "←" D8 is added to the urine quantitative measurement value. In addition, in the case where the urine quantitative sample adjustment condition is changed from the usual adjustment condition to the changed adjustment condition at the time of the urine quantitative measurement, a sign "*" D9 is added to the urine quantitative measurement value.

FIG. 13 shows another example of the examination report. In an examination report 8B, the urine qualitative measurement value of the measurement item P/C is "DILUTE". In this case, since the urine qualitative measurement value is an abnormal value, the sign "!" D6 is added to "DILUTE". In the case where the urine qualitative measurement value is "DILUTE", re-measurement is required. In this case, the judgment section 69b automatically judges that the urine quantitative measurement is performed, and hence the sign "←" D8 is added to the urine quantitative measurement values of PRO and CRE in addition to P/C. The change of the urine quantitative sample adjustment condition is not performed, and hence the sign indicative of that is not added.

FIG. 14 shows another example of the examination report. In an examination report 8C, a note D10 denoting that the judgment that the urine quantitative measurement of GLU and PRO is necessary has been automatically performed is described in the margin. In addition, a note D11 denoting that the change of the urine quantitative sample adjustment condition has been performed on the measurement item PRO is described below the note D10. On the other hand, in an examination report 8D shown in FIG. 15, a note D12 denoting that there is no item of which the urine quantitative measurement is judged to be necessary is described in the margin. In addition, below the note D12, a note D13 denoting that the change of the urine quantitative sample adjustment condition has not been performed is described.

Note that, in the present embodiment, the measurement item comparison table T1, the urine quantitative measurement necessity determination table T2, the urine quantitative measurement item classification table T3, and the urine quantitative sample adjustment criterion T4 have been described by taking the preset configuration as an example, but a configuration in which a user or the like can appropriately modify or add the measurement item, the measurement range, and the numerical value in T1 to T4 may also be adopted. In this case, even in the case where the measurement method and the condition of the urine qualitative measurement or the urine quantitative measurement are changed, it is possible to easily cope with the change.

According to the present embodiment, in the case where the urine quantitative measurement of the measurement item is performed subsequently to the urine qualitative measurement, the determination section 69a predicts the urine quantitative measurement value that will be acquired by the urine quantitative measurement device M2 later based on the level of the urine qualitative measurement result acquired earlier by the urine qualitative measurement device M1, and selects and determines the urine quantitative sample adjustment condition that allows proper urine quantitative measurement. With this, it is possible to appropriately avert an event that it is not possible to accurately perform the urine quantitative measurement of a high-concentration area due to saturation of the measurement value in the urine quantitative measurement, and the occurrence of the prozone-like phenomenon. Accordingly, it is possible to reduce the frequency of re-measurement of the urine quantitative measurement. Therefore, in the case where the urine quantitative measurement of the measurement item of the urine sample U is performed subsequently to the urine qualitative measurement, it is possible to achieve a reduction in time required for the urine quantitative measurement and a reduction in measurement cost.

According to the present embodiment, the judgment section 69b automatically judges whether or not the urine quantitative measurement is performed based on the level of the urine qualitative measurement result acquired earlier by the urine qualitative measurement device M1. With this, the examiner does not need to operate, e.g., the information processing device 6 to check the urine qualitative measurement result and determine whether or not the urine quantitative measurement is performed. In this respect, the measurement system MS1 can reduce the burden of the examiner.

According to the present embodiment, the determination section 69a automatically determines the urine quantitative sample adjustment condition corresponding to the level of the urine qualitative measurement result before the urine quantitative measurement is performed based on the urine quantitative sample adjustment criterion T4 in which the urine quantitative sample adjustment condition including at least one combination of the urine sample quantity, the dilution liquid quantity, and the liquid reagent quantity is described. With this, labor of the examiner required to discuss causes and measures in the case where the execution of the urine quantitative measurement is unsuccessful is reduced. Therefore, with this, it is also possible to achieve a reduction in the burden of the examiner.

In the present embodiment, when the examination reports 8A to 8D are prepared, the examiner that uses the measurement system MS1 can easily and speedily realize the presence or absence of the automatic judgment of the urine quantitative measurement or the change of the urine quantitative sample adjustment condition. Consequently, the examiner does not need to operate, e.g., the information processing device 6 to check the above information, and it is possible to achieve a reduction in the burden of the examiner.

According to the present embodiment, the measurement items of the urine quantitative measurement device M2 are classified as the first to third classifications in advance. In the case where the measurement item belongs to the first classification, the determination section 69a determines whether or not the urine quantitative sample adjustment condition is changed based on the level of the urine qualitative measurement result. With this, it is not necessary to determine the necessity to change the urine quantitative sample adjustment condition on all of the measurement items, and hence it is possible to reduce the burden of the determination section 69a, and achieve an improvement in throughput or prevent a reduction in throughput. Note that, instead of performing the determination according to whether or not the measurement item belongs to the first classification, a configuration may also be adopted in which the necessity to change the urine quantitative sample adjustment condition is determined on all of the measurement items.

Second Embodiment

Figure 16:
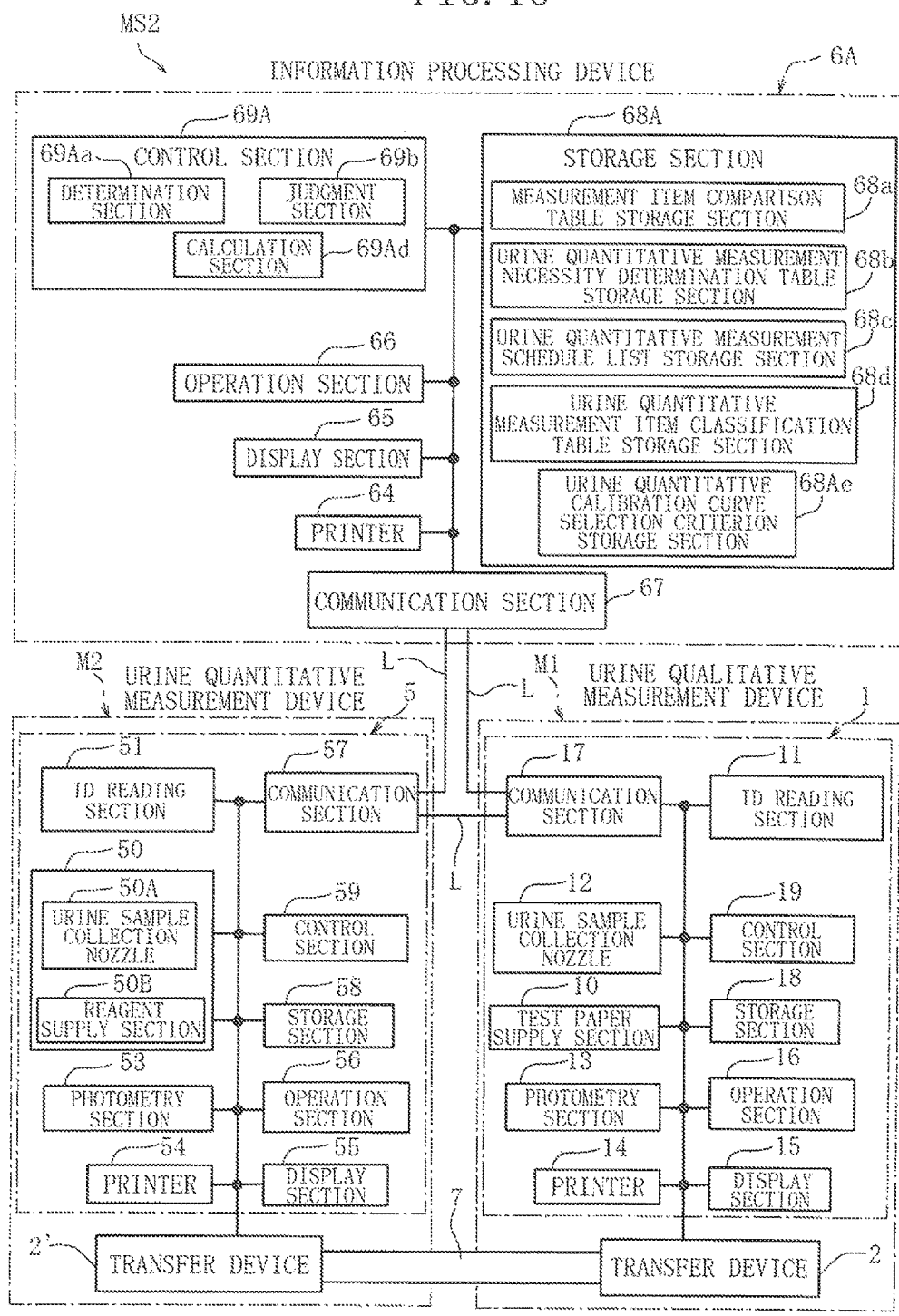
FIG. 16 is a block diagram showing the measurement system according to a second embodiment of the present invention.

FIG. 16 shows another embodiment of the measurement system according to the present invention. In the drawing, elements identical or similar to those in the first embodiment are designated by the same reference numerals as those in the first embodiment. The detailed description of the elements designated by the same reference numerals will be omitted.

As shown in FIG. 16, a measurement system MS2 includes the urine qualitative measurement device M1, the urine quantitative measurement device M2, and an information processing device 6A. Similarly to the measurement system MS1, the measurement system MS2 is installed in, e.g., a laboratory of a hospital, and is used to perform the urine quantitative measurement subsequently to the urine qualitative measurement of the measurement item of the urine sample U is performed. The measurement system MS2 is different from the measurement system MS1 in that the measurement system MS2 has a urine quantitative calibration curve selection criterion storage section 68Ae in a storage section 68A. In addition, correspondingly to that, the measurement system MS2 is different from the measurement system MS1 in that a control section 69A has a determination section 69Aa and a calculation section 69Ad.

The urine sample U corresponds to an example of the biological sample in the present invention. Examples of the biological sample that can be measured in the measurement system MS2 include feces, blood serum, blood plasma, and whole blood in addition to the urine sample U. With regard to the feces, a liquid obtained by filtering a suspension in which the feces are suspended is used as the sample.

As shown in FIG. 17, the urine quantitative calibration curve selection criterion storage section 68Ae stores a urine quantitative calibration curve selection criterion T5. In the urine quantitative calibration curve selection criterion T5, a urine quantitative calibration curve to be selected is described for each measurement item. As the urine quantitative calibration curve, a usual calibration curve that is usually used and a changed calibration curve that is selected in the case where the usual calibration curve cannot be used are prepared for each selected item. In the case where the measurement item belongs to the first classification, the determination section 69Aa determines whether or not the change of the urine quantitative calibration curve is necessary based on the level of the urine qualitative measurement value. The urine quantitative calibration curve selection criterion storage section 68Ae corresponds to an example of a quantitative calibration curve selection criterion storage section in the present invention. The urine quantitative calibration curve selection criterion T5 corresponds to an example of a quantitative calibration curve selection criterion in the present invention. In addition, the urine quantitative calibration curve corresponds to an example of a quantitative calibration curve in the present invention.

In the urine quantitative calibration curve selection criterion T5, in the measurement item GLU belonging to the first classification, for example, the usual calibration curve applied in the case where the urine qualitative measurement result is from − to 2+ and the changed calibration curve applied in the case where the urine qualitative measurement result is not less than 3+ are prepared. Therefore, a threshold value is set between the qualitative value +2 and the qualitative value +3. The usual calibration curve is set as a default calibration curve when, e.g., the measurement system MS2 is activated. The usual calibration curve has properties that its measurement range is narrow, but its dynamic range is large and simultaneous reproducibility is excellent. In contrast to this, the changed calibration curve has properties that its measurement range is wider than that of the usual calibration curve, but its dynamic range in low concentrations is small and the simultaneous reproducibility is slightly inferior to that of the usual calibration curve. When the usual calibration curve is used, there are cases where measurement of a high-concentration area cannot be performed or the prozone-like phenomenon occurs. In such cases, when the changed calibration curve is selected, the above problem is solved. In the measurement item PRO as well, from the same viewpoint as that in the case of GLU, the usual calibration curve and the changed calibration curve are prepared. Note that the number of kinds of the changed calibration curve does not need to be one. A plurality of the changed calibration curves may be prepared and the proper changed calibration curve may be selected from them.

On the other hand, in the measurement item CRE belonging to the second classification, it is not necessary to change the usual calibration curve set as the default calibration curve for the above reason. Accordingly, only the usual calibration curve is described in the urine quantitative calibration curve selection criterion. For ALB that is classified as the second classification similarly to CRE, only the usual calibration curve is prepared from the same viewpoint as that in the case of CRE.

In addition, in the measurement items AMY, NAG, and BMG classified as the third classification, it is not necessary to change the calibration curve. Therefore, in these measurement items, only the usual calibration curve is described in the urine quantitative calibration curve selection criterion (not shown).

Note that, it is also possible to adopt a configuration in which the usual calibration curve or the changed calibration curve is selected for each measurement without using the usual calibration curve as the default calibration curve.

In addition, the urine quantitative calibration curve selection criterion T5 has been described by taking the preset configuration as an example, but a configuration may also be adopted in which the user or the like can appropriately modify the urine quantitative calibration curve selection criterion T5 or additionally set the calibration curve.

Next, a description will be given of an example of the operation process procedures of the measurement system MS2 by the control section 69A of the information processing device 6A with reference to flowcharts shown in FIGS. 18 and 19, FIG. 6, and FIGS. 16 and 17. Note that, in FIGS. 18 and 19, procedures identical or similar to those in the first embodiment are omitted or designated by the same reference numerals. The detailed description of the procedures that are omitted or designated by the same reference numerals will be omitted.

When the urine quantitative measurement urine sample U is collected by the urine sample collection nozzle 50A (S7), the control section 69A refers to the urine quantitative measurement schedule list based on the subject identification information, and causes the urine quantitative measurement device M2 to perform the urine quantitative measurement of the required measurement item in accordance with the description of the list (S8A). The urine quantitative measurement of each measurement item is performed in accordance with a subroutine shown in FIG. 19.

In the case where it is determined that the measurement item belongs to the first classification, the determination section 69Aa refers to the urine quantitative calibration curve selection criterion T5 shown in FIG. 17, and determines whether or not the change of the urine quantitative calibration curve is necessary based on the level of the urine qualitative measurement value (S802: YES, S803A).

In the case where the determination section 69Aa determines that the change thereof is necessary, the determination section 69Aa refers to the urine quantitative calibration curve selection criterion T5 shown in FIG. 17, and determines that the usual calibration curve is changed to the changed calibration curve (S804: YES, S805A). Next, the urine sample collection nozzle 50A dispenses a predetermined quantity of the urine sample U to the reaction cell 53b. In addition, the reagent dispensing nozzle 50Ba dispenses a predetermined quantity of the dilution liquid and a predetermined quantity of the liquid reagent to the reaction cell 53b (S806A).

The photometry section 53 detects the color developed in the reaction cell 53b as the absorbance (S807). The absorbance corresponds to an example of a urine quantitative response value. In addition, the absorbance corresponds to an example of a quantitative response value in the present invention. The calculation section 69Ac applies the absorbance to the changed calibration curve to thereby calculate the urine quantitative measurement concentration of a predetermined component in the urine (S808A). The urine quantitative measurement concentration of the predetermined component corresponds to an example of the urine quantitative measurement value. In addition, the urine quantitative measurement concentration of the predetermined component corresponds to an example of the quantitative measurement value in the present invention.

In the case where the determination section 69Aa determines that the measurement item does not belong to the first classification (S802: NO), and determines that the measurement item belongs to the second classification (S809: YES), or in the case where the determination section 69Aa determines that the measurement item does not belong to the second classification, and determines that the measurement item belongs to the third classification (S809: NO, S810), the determination section 69Aa determines that the usual calibration curve is used as the urine quantitative calibration curve (S811A). In addition, in the case where the determination section 69Aa determines that it is not necessary to change the urine quantitative calibration curve in the measurement item belonging to the first classification (S804: NO), the same measures are taken (S811A). In these measurement items, the dispensing of the predetermined quantity of the urine sample U to the reaction cell 53b, the dispensing of the liquid reagent and the like, and the measurement of the absorbance by the photometry section 53 are performed (S811A, S812). Next, the calculation section 69Ac applies the absorbance to the usual calibration curve to thereby calculate the urine quantitative measurement concentration of the predetermined component in the urine (S813A).

Figure 18:
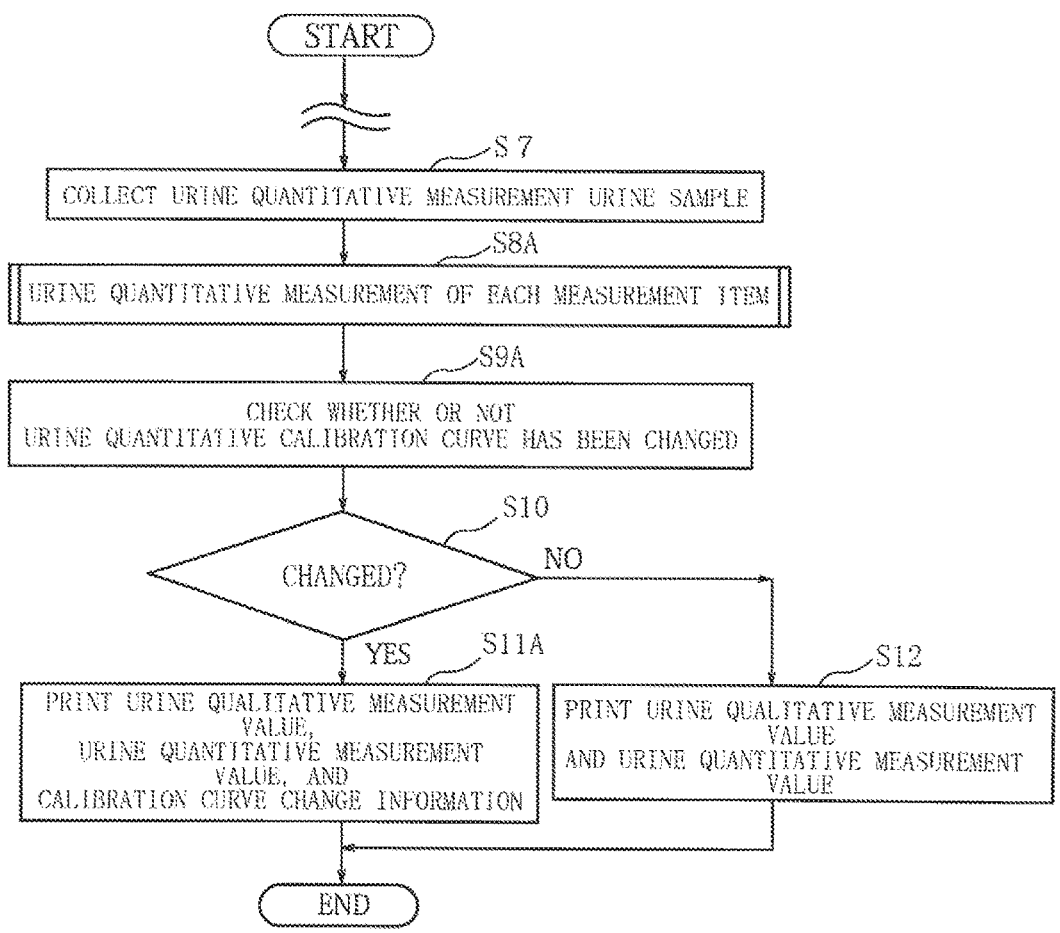
FIG. 18 is a flowchart showing an example of the operation process procedures of the control section of the measurement system shown in FIG. 16.
Figure 19:
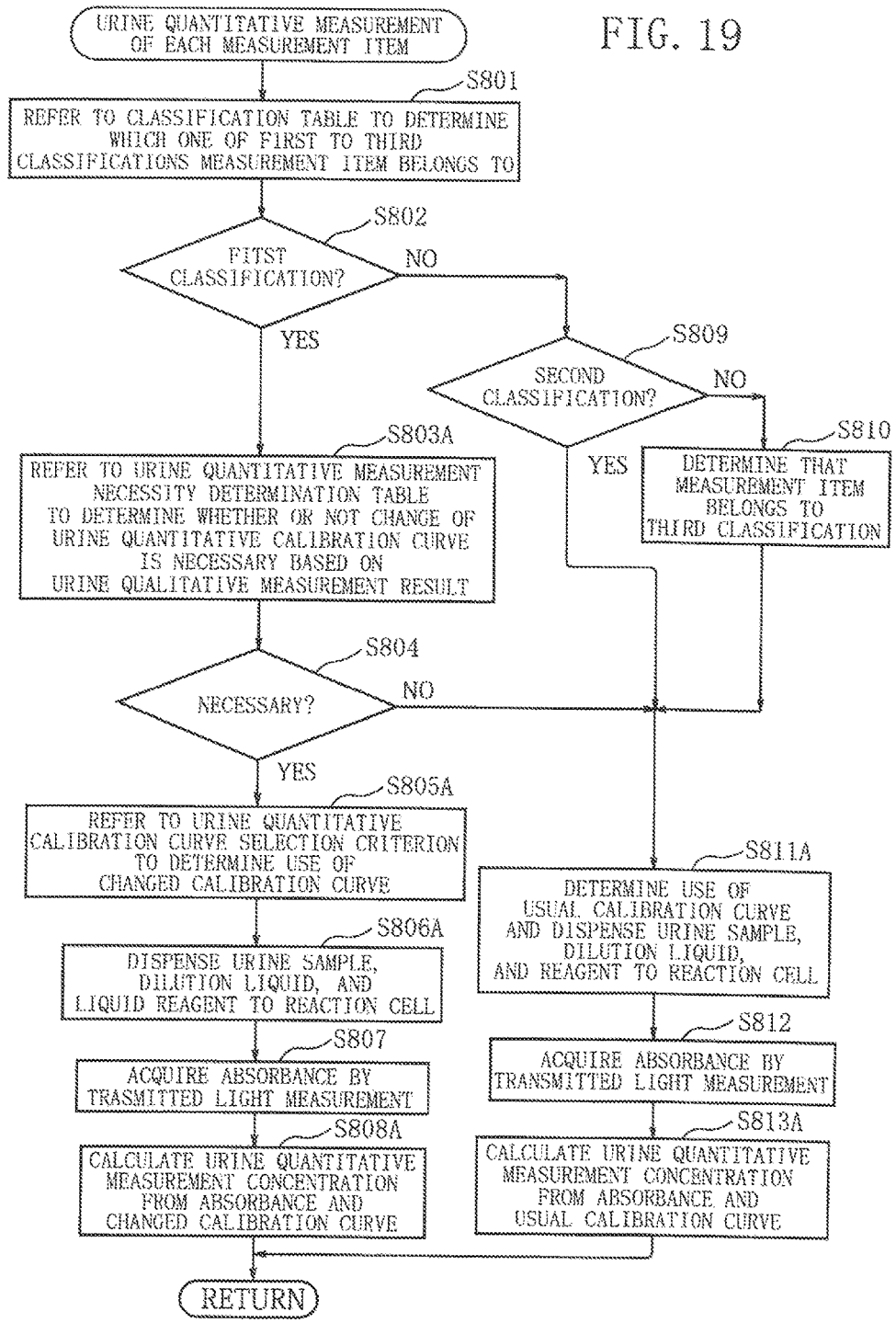
FIG. 19 is a flowchart showing an example of the urine quantitative measurement subroutine of each measurement item in the flowchart shown in FIG. 17.

At the point of time when these processes are completed, the procedures return to the operation process of the flowchart shown in FIG. 18.

Note that it is also possible to adopt a configuration in which the urine quantitative calibration curve selection criterion T5 is consulted for each measurement and the usual calibration curve or the changed calibration curve is selected without using the usual calibration curve as the default calibration curve.

Next, in the flowchart shown in FIG. 18, the control section 69A checks whether or not the urine quantitative calibration curve has been changed in the urine quantitative measurement (S9A). In the case where it is determined that the urine quantitative calibration curve has been changed (S10: YES), the printer 64 prints the urine qualitative measurement value, the urine quantitative measurement value, and urine quantitative calibration curve change information on a predetermined examination report in association with the subject identification information, and outputs the examination report (S11A). On the other hand, in the case where the urine quantitative calibration curve is not changed (S10: NO), the printer 64 prints the urine qualitative measurement value and the urine quantitative measurement value (S12). In this case, the urine quantitative calibration curve change information is not printed, or information indicating that the urine quantitative calibration curve is not changed is printed.

According to the present embodiment, it is possible to reduce the frequency of re-measurement of the urine quantitative measurement, and achieve a reduction in time required for the quantitative measurement and a reduction in measurement cost. In addition, the determination section 69Aa automatically determines the urine quantitative calibration curve corresponding to the level of the urine qualitative measurement result from the urine quantitative calibration curve selection criterion in which the urine quantitative calibration curve is described before the urine quantitative measurement is performed. Accordingly, labor of the examiner required to discuss causes and measures in the case where the execution of the urine quantitative measurement is unsuccessful is reduced. With this, it is possible to achieve a reduction in the burden of the examiner.

According to the present embodiment, the calibration curve for calculating the urine quantitative measurement value from the absorbance acquired by the urine quantitative measurement device M2 is changed. Accordingly, the correction that uses the arithmetic operation parameter after the calculation of the urine quantitative measurement value is not necessary. With this, it is possible to achieve a reduction in the burden of the control section 69A.

The present invention is not limited to the contents of the embodiments described above.

In the first and second embodiments, the description has been made by taking the measurement system configured by connecting the urine qualitative measurement device, the urine quantitative measurement device, and the information processing device with the communication line as an example, but the measurement system of the present invention is not limited to the above configuration. The measurement system may also be configured such that the urine qualitative measurement device, the urine quantitative measurement device, and the information processing device are put in one case as an integral device. In addition, the measurement system of the present invention can be configured to include a device into which the urine qualitative measurement device and the urine quantitative measurement device are integrated and the information processing device. Further, the measurement system of the present invention may also be configured such that one of the urine qualitative measurement device and the urine quantitative measurement device and the information processing device are integrated into one device. In this case, the urine qualitative measurement device M1 or the urine quantitative measurement device M2 includes the control section 69. With this configuration, commonality of duplicate elements such as the printer, the display section, the operation section, the ID reading section, the storage section, and the control section can be achieved. With this, it is possible to achieve a reduction in the size of the measurement system and a reduction in manufacturing cost. In the case where the information processing device 6 is not present, data exchange is performed between the urine qualitative measurement device M1 and the urine quantitative measurement device M2.

In the first and second embodiments, it is possible to appropriately change the flow after the urine qualitative measurement. For example, before the collection of the urine quantitative measurement sample (S7), the determination of the necessity to change the urine quantitative sample adjustment condition (S801 to S805) may be performed. In addition, without performing the collection of the urine quantitative measurement sample (S7), the sample may be collected directly from the urine sample container 30, and the urine quantitative sample may be adjusted (S806).

In the first and second embodiments, the description has been made by taking the case where the concentration is calculated based on the optical response values such as the reflectance and the absorbance as an example. However, the present invention can be applied also to the case where the concentration is calculated based on an electric response value when a voltage is applied to a reaction system or a current is caused to flow to the reaction system depending on the type of the reaction system. In addition, it is possible to appropriately change the reagent, the measurement method, and the measurement condition used in the urine qualitative measurement and the urine quantitative measurement to those other than the reagent, the measurement method, and the measurement condition described above.

In the embodiments described above, the description has been made by taking the urine specimen as an example of the biological sample, but the present invention can also be applied to the measurement of not only the urine specimen but also a blood specimen. The qualitative measurement in the blood specimen includes the measurement that uses a test paper or an immunochromatograph. For example, in the blood sample, the qualitative measurement of a hepatitis virus such as HCV or HBs may be performed by using the immunochromatograph, and the quantitative measurement may be performed by using a particle agglutination method (PA method) or chemiluminescent immunoassay (CLIA method) after it is determined whether or not a quantitative sample adjustment criterion can be changed by referring to the quantitative sample adjustment criterion. In addition, the qualitative measurement may be performed by using the test paper for blood urea nitrogen measurement, and the quantitative measurement may be performed by using an urease method after it is determined whether or not the quantitative sample adjustment criterion can be changed by referring to the quantitative sample adjustment criterion. Further, the description has been made by taking the measurement that uses the urine test paper as an example of the urine qualitative measurement, but erythrocyte or the like may be measured by, e.g., urinary sediment measurement, the quantitative sample adjustment condition may be determined by referring to the quantitative sample adjustment criterion based on the result, and the quantitative measurement may be performed.

In the quantitative measurement device, it is possible to adopt a configuration in which the selection of the quantitative sample adjustment condition is combined with the selection of the quantitative calibration curve. According to this configuration, it is possible to control the quantitative measurement more minutely.

What is claimed is:

1. A measurement system for performing qualitative measurement and quantitative measurement of a measurement item of a biological sample, the measurement system comprising:
   a quantitative sample adjustment criterion storage configured to store a quantitative sample adjustment criterion corresponding to a qualitative measurement result in the qualitative measurement;
   a qualitative measurer configured to acquire the qualitative measurement result of the measurement item by performing the qualitative measurement on the biological sample;
   a determinator configured to determine a proper quantitative sample adjustment condition;
   an adjustor configured to adjust the biological sample for use in the quantitative measurement; and
   a quantitative measurer configured to acquire a quantitative measurement value of the measurement item by performing the quantitative measurement on the biological sample that is for use in the quantitative measurement and has been adjusted by the adjustor, wherein
   the determinator is configured to determine a dilution factor of the biological sample by referring to the quantitative sample adjustment criterion based on the qualitative measurement result to determine necessity to change the dilution factor of the biological sample, and
   the adjustor is configured to adjust the biological sample for use in the quantitative measurement based on the dilution factor of the biological sample determined by the determinator.

2. The measurement system according to claim 1, further comprising a judger configured to judge whether or not the quantitative measurement is performed based on the qualitative measurement result acquired by the qualitative measurer.

3. The measurement system according to claim 1, wherein the measurement item is classified as a first classification that requires determination of the quantitative sample adjustment condition corresponding to the qualitative measurement result or a second classification that does not require the determination of the quantitative sample adjustment condition corresponding to the qualitative measurement result in the quantitative sample adjustment criterion.

4. The measurement system according to claim 3, wherein the measurement item classified as the first classification has a measurement range of the quantitative measurement that is narrower than a corresponding measurement range of the qualitative measurement, and the measurement item classified as the second classification has a measurement range of the quantitative measurement that is wider than or equal to a corresponding measurement range of the qualitative measurement.

5. The measurement system according to claim 3, wherein the first classification includes a prozone-like phenomenon occurrence measurement item in which a prozone-like phenomenon occurs in the quantitative measurement.

6. The measurement system according to claim 5, wherein the prozone-like phenomenon occurrence measurement item is a protein quantity measurement.

7. The measurement system according to claim 1, further comprising:
   an arithmetic operation parameter storage configured to store an arithmetic operation parameter corresponding to the quantitative sample adjustment condition; and
   an arithmetic operation configured to correct the quantitative measurement value based on the arithmetic operation parameter.

8. The measurement system according to claim 1, further comprising an output configured to output an examination report in which the quantitative measurement value is described, wherein
   the output is configured to describe quantitative sample adjustment condition change information in the examination report in a case where the determinator has changed the quantitative sample adjustment condition.

* * * * *